(12) United States Patent
Neelam Jagadish et al.

(10) Patent No.: US 12,154,673 B2
(45) Date of Patent: Nov. 26, 2024

(54) ARTIFICIAL INTELLIGENCE ASSISTED HOME THERAPY SETTINGS FOR DIALYSIS

(71) Applicant: MOZARC MEDICAL US LLC, Minneapolis, MN (US)

(72) Inventors: Rajalakshmi Neelam Jagadish, Bangalore (IN); Sandesh Dasharath Gavade, Bangalore (IN)

(73) Assignee: MOZARC MEDICAL US LLC, Minneapolis, MN (US)

( * ) Notice: Subject to any disclaimer, the term of this patent is extended or adjusted under 35 U.S.C. 154(b) by 596 days.

(21) Appl. No.: 17/391,525

(22) Filed: Aug. 2, 2021

(65) Prior Publication Data
US 2023/0036006 A1  Feb. 2, 2023

(51) Int. Cl.
*G05B 13/02* (2006.01)
*A61M 1/16* (2006.01)
(Continued)

(52) U.S. Cl.
CPC .......... *G16H 20/40* (2018.01); *A61M 1/1601* (2014.02); *G06N 20/00* (2019.01); *G16H 20/17* (2018.01);
(Continued)

(58) Field of Classification Search
CPC .................................................. G05B 13/024
See application file for complete search history.

(56) References Cited

U.S. PATENT DOCUMENTS 3,602,222 A   8/1971 Herndon
3,608,729 A   9/1971 Haselden
(Continued)

FOREIGN PATENT DOCUMENTS

CA   3149888 A1 * 3/2021  ............. A61B 5/165
CN   1643368 A    7/2005
(Continued)

OTHER PUBLICATIONS

Heiko Hickstein, Et Al; "Clinical application of fuzzy-controlled blood pressure stabilization in patients prone to hypotension duirng hemodiaylsis", Dyalysis & Transplantation, vol. 38, No. 2, Feb. 1, 2009, pp. 58-64.
(Continued)

*Primary Examiner* — Suresh Suryawanshi

(57) ABSTRACT

A medical device is provided, including: a therapeutic subsystem to deliver a medical therapy, including a sensor to monitor a biometric health factor; a user interface; a controller, including a processor and a memory; therapy software including instructions encoded within the memory to instruct the processor to receive a prescribed therapy, to receive a therapeutic setting recommendation, and to display the therapeutic setting recommendation to an operator via the user interface; a network interface, and instructions to receive, via the network interface, a prepared artificial intelligence (AI) model from a cloud service; and an AI circuit having execution hardware including at least one logic gate, and further including instructions to instruct the execution hardware to execute the prepared AI model to provide a recommended therapy setting for the therapeutic subsystem, wherein the circuit is further to incorporate into the prepared AI model data from the sensor.

20 Claims, 9 Drawing Sheets

(51) Int. Cl.
  *G06N 20/00* (2019.01)
  *G16H 20/17* (2018.01)
  *G16H 20/40* (2018.01)

(52) U.S. Cl.
  CPC .............. *A61M 2205/3334* (2013.01); *A61M 2205/3553* (2013.01); *A61M 2205/502* (2013.01); *A61M 2205/52* (2013.01); *A61M 2230/04* (2013.01); *G05B 13/024* (2013.01)

(56) References Cited

U.S. PATENT DOCUMENTS

| | | |
|---|---|---|
| 3,669,878 A | 6/1972 | Marantz |
| 3,669,880 A | 6/1972 | Marantz |
| 3,730,183 A | 5/1973 | Goldsmith |
| 3,754,867 A | 8/1973 | Guenther |
| 3,850,835 A | 11/1974 | Marantz |
| 3,884,808 A | 5/1975 | Scott |
| 3,989,622 A | 11/1976 | Marantz |
| 3,989,625 A | 11/1976 | Mason |
| 4,060,485 A | 11/1977 | Eaton |
| 4,371,385 A | 2/1983 | Johnson |
| 4,374,382 A | 2/1983 | Markowitz |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |
| 4,581,141 A | 4/1986 | Ash |
| 4,650,587 A | 3/1987 | Polak |
| 4,661,246 A | 4/1987 | Ash |
| 4,678,408 A | 7/1987 | Mason |
| 4,685,903 A | 8/1987 | Cable |
| 4,747,822 A | 5/1988 | Peabody |
| 4,750,494 A | 6/1988 | King |
| 4,772,560 A | 9/1988 | Attar |
| 4,799,493 A | 1/1989 | DuFault |
| 4,826,663 A | 5/1989 | Alberti |
| 4,828,693 A | 5/1989 | Lindsay |
| 4,976,683 A | 12/1990 | Gauthier |
| 5,032,265 A | 7/1991 | Jha |
| 5,080,653 A | 1/1992 | Voss |
| 5,091,642 A | 2/1992 | Chow |
| 5,092,838 A | 3/1992 | Faict |
| 5,092,886 A | 3/1992 | Dobos-Hardy |
| 5,097,122 A | 3/1992 | Coiman |
| 5,127,404 A | 7/1992 | Wyborny |
| 5,141,493 A | 8/1992 | Jacobsen |
| 5,284,470 A | 2/1994 | Beltz |
| 5,302,288 A | 4/1994 | Meidl |
| 5,305,745 A | 4/1994 | Zacouto |
| 5,318,750 A | 6/1994 | Lascombes |
| 5,364,593 A | 11/1994 | Mihaylov |
| 5,415,838 A | 5/1995 | Rieger |
| 5,468,388 A | 11/1995 | Goddard |
| 5,507,723 A | 4/1996 | Keshaviah |
| 5,643,201 A | 7/1997 | Peabody |
| 5,651,893 A | 7/1997 | Kenley |
| 5,683,432 A | 11/1997 | Goedeke |
| 5,744,031 A | 4/1998 | Bene |
| 5,762,782 A | 6/1998 | Kenley |
| 5,819,007 A | 10/1998 | Elghazzawi |
| 5,902,336 A | 5/1999 | Mishkin |
| 5,944,684 A | 8/1999 | Roberts |
| 5,987,352 A | 11/1999 | Klein |
| 6,042,721 A | 3/2000 | Peters |
| 6,048,732 A | 4/2000 | Anslyn |
| 6,052,622 A | 4/2000 | Holmstrom |
| 6,058,331 A | 5/2000 | King |
| 6,156,002 A | 12/2000 | Polaschegg |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,505,075 B1 | 1/2003 | Weiner |
| 6,554,798 B1 | 4/2003 | Mann |
| 6,555,986 B2 | 4/2003 | Moberg |
| 6,589,229 B1 | 7/2003 | Connelly |
| 6,602,399 B1 | 8/2003 | Fromherz |
| 6,609,023 B1 | 8/2003 | Fischell |
| 6,627,164 B1 | 9/2003 | Wong |
| 6,645,191 B1 | 11/2003 | Knerr |
| 6,676,608 B1 | 1/2004 | Keren |
| 6,689,083 B1 | 2/2004 | Gelfand |
| 6,706,007 B2 | 3/2004 | Gelfand |
| 6,711,439 B1 | 3/2004 | Bradley |
| 6,726,647 B1 | 4/2004 | Sternby |
| 6,780,322 B1 | 8/2004 | Bissler |
| 6,818,196 B2 | 11/2004 | Wong |
| 6,878,283 B2 | 4/2005 | Thompson |
| 6,887,214 B1 | 5/2005 | Levin |
| 6,890,315 B1 | 5/2005 | Levin |
| 6,960,179 B2 | 11/2005 | Gura |
| 7,074,332 B2 | 7/2006 | Summerton |
| 7,077,819 B1 | 7/2006 | Goldau |
| 7,131,956 B1 | 11/2006 | Pirazzoli |
| 7,175,809 B2 | 2/2007 | Gelfand |
| 7,207,946 B2 | 4/2007 | Sirokman |
| 7,208,092 B2 | 4/2007 | Micheli |
| 7,276,042 B2 | 10/2007 | Polaschegg |
| 7,399,289 B2 | 7/2008 | Gelfand |
| 7,404,799 B1 | 7/2008 | Koh |
| 7,500,958 B2 | 3/2009 | Asbrink |
| 7,566,432 B2 | 7/2009 | Wong |
| 7,575,564 B2 | 8/2009 | Childers |
| 7,610,086 B1 | 10/2009 | Ke |
| 7,674,231 B2 | 3/2010 | McCombie |
| 7,704,361 B2 | 4/2010 | Garde |
| 7,736,507 B2 | 6/2010 | Wong |
| 7,744,553 B2 | 6/2010 | Kelly |
| 7,754,852 B2 | 7/2010 | Burnett |
| 7,756,572 B1 | 7/2010 | Fard |
| 7,775,983 B2 | 8/2010 | Zhang |
| 7,775,986 B2 | 8/2010 | Roeher |
| 7,776,210 B2 | 8/2010 | Rosenbaum |
| 7,785,463 B2 | 8/2010 | Bissler |
| 7,794,141 B2 | 9/2010 | Perry |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum |
| 7,955,291 B2 | 6/2011 | Sternby |
| 7,967,022 B2 | 6/2011 | Grant |
| 7,981,082 B2 | 7/2011 | Wang |
| 8,000,000 B2 | 8/2011 | Greenberg |
| 8,034,161 B2 | 10/2011 | Gura |
| 8,070,709 B2 | 12/2011 | Childers |
| 8,096,969 B2 | 1/2012 | Roberts |
| 8,105,260 B2 | 1/2012 | Tonelli |
| 8,202,503 B2 | 2/2012 | Putnam |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,282,828 B2 | 10/2012 | Wallenas |
| 8,292,594 B2 | 10/2012 | Tracey |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,404,091 B2 | 3/2013 | Ding |
| 8,409,441 B2 | 4/2013 | Wilt |
| 8,496,809 B2 | 7/2013 | Roger |
| 8,499,780 B2 | 8/2013 | Wilt |
| 8,500,676 B2 | 8/2013 | Jansson |
| 8,512,271 B2 | 8/2013 | Moissl |
| 8,518,260 B2 | 8/2013 | Raimann |

(56) References Cited

U.S. PATENT DOCUMENTS

| | | |
|---|---|---|
| 8,521,482 B2 | 8/2013 | Akonur |
| 8,535,525 B2 | 9/2013 | Heyes |
| 8,560,510 B2 | 10/2013 | Brueggerhoff |
| 8,580,112 B2 | 11/2013 | Updyke |
| 8,597,227 B2 | 12/2013 | Childers |
| 8,696,626 B2 | 4/2014 | Kirsch |
| 8,903,492 B2 | 12/2014 | Soykan |
| 8,926,542 B2 | 1/2015 | Gerber |
| 9,700,663 B2 | 7/2017 | Burbank |
| 9,907,897 B2 | 3/2018 | Burbank |
| 10,076,599 B2 | 9/2018 | Eyrard |
| 10,076,735 B2 | 9/2018 | Jansson |
| 10,173,881 B2 | 1/2019 | Beavis |
| 10,459,459 B2 | 10/2019 | Beavis |
| 10,478,544 B2 | 11/2019 | Friederichs |
| 10,610,630 B2 | 4/2020 | Burbank |
| 2001/0048637 A1 | 12/2001 | Weigl |
| 2002/0016550 A1 | 2/2002 | Sweeney |
| 2002/0042561 A1 | 4/2002 | Schulman |
| 2002/0112609 A1 | 8/2002 | Wong |
| 2003/0028089 A1 | 4/2003 | Galley |
| 2003/0069481 A1 | 4/2003 | Hervy |
| 2003/0080059 A1 | 5/2003 | Peterson |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0187479 A1 | 10/2003 | TranThong |
| 2004/0019312 A1 | 1/2004 | Childers |
| 2004/0060865 A1 | 4/2004 | Callan |
| 2004/0068219 A1 | 4/2004 | Summerton |
| 2004/0099593 A1 | 5/2004 | DePaolis |
| 2004/0147900 A1 | 7/2004 | Polaschegg |
| 2004/0168969 A1 | 9/2004 | Sternby |
| 2004/0215090 A1 | 10/2004 | Erkkila |
| 2005/0065760 A1 | 3/2005 | Murtfeldt |
| 2005/0113796 A1 | 5/2005 | Taylor |
| 2005/0126961 A1 | 6/2005 | Bissler |
| 2005/0131331 A1 | 6/2005 | Kelly |
| 2005/0126998 A1 | 7/2005 | Childers |
| 2005/0150832 A1 | 7/2005 | Tsukamoto |
| 2005/0214863 A1 | 9/2005 | McDevitt |
| 2005/0234354 A1 | 10/2005 | Rowlandson |
| 2005/0234357 A1 | 10/2005 | Xue |
| 2005/0234381 A1 | 10/2005 | Niemetz |
| 2005/0234534 A1 | 10/2005 | Rowlandson |
| 2005/0236330 A1 | 10/2005 | Nier |
| 2005/0265895 A1 | 12/2005 | Kopelman |
| 2005/0274658 A1 | 12/2005 | Rosenbaum |
| 2006/0025661 A1 | 2/2006 | Sweeney |
| 2006/0025748 A1 | 2/2006 | Ye |
| 2006/0217771 A1 | 2/2006 | Soykan |
| 2006/0058731 A1 | 3/2006 | Burnett |
| 2006/0191850 A1 | 8/2006 | Bosetto |
| 2006/0195064 A1 | 8/2006 | Plahey |
| 2006/0226079 A1 | 10/2006 | Mori |
| 2006/0241709 A1 | 10/2006 | Soykan |
| 2006/0247548 A1 | 11/2006 | Sarkar |
| 2006/0264894 A1 | 11/2006 | Moberg |
| 2007/0007208 A1 | 1/2007 | Brugger |
| 2007/0031972 A1 | 2/2007 | Attar |
| 2007/0038138 A1 | 2/2007 | Gill |
| 2007/0066928 A1 | 3/2007 | Lannoy |
| 2007/0073168 A1 | 3/2007 | Zhang |
| 2007/0138011 A1 | 6/2007 | Hofmann |
| 2007/0161113 A1 | 7/2007 | Ash |
| 2007/0175827 A1 | 8/2007 | Wariar |
| 2007/0179431 A1 | 8/2007 | Roberts |
| 2007/0213653 A1 | 9/2007 | Childers |
| 2007/0215545 A1 | 9/2007 | Bissler |
| 2007/0222992 A1 | 9/2007 | Oda |
| 2007/0255250 A1 | 11/2007 | Moberg |
| 2007/0276270 A1 | 11/2007 | Tran |
| 2008/0006570 A1 | 1/2008 | Gura |
| 2008/0021337 A1 | 1/2008 | Li |
| 2008/0053905 A9 | 3/2008 | Brugger |
| 2008/0067132 A1 | 3/2008 | Ross |
| 2008/0093276 A1 | 4/2008 | Roger |
| 2008/0200866 A1 | 8/2008 | Prisco |
| 2008/0215247 A1 | 9/2008 | Tonelli |
| 2008/0233008 A1 | 9/2008 | Sarkisov |
| 2008/0253427 A1 | 10/2008 | Kamen |
| 2009/0020471 A1 | 1/2009 | Tsukamoto |
| 2009/0036825 A1 | 2/2009 | Petersen |
| 2009/0101577 A1 | 4/2009 | Fulkerson |
| 2009/0124869 A1 | 5/2009 | Hu |
| 2009/0124963 A1 | 5/2009 | Hogard |
| 2009/0127193 A1 | 5/2009 | Updyke |
| 2009/0149776 A1 | 6/2009 | Adams |
| 2009/0171261 A1 | 7/2009 | Sternby |
| 2009/0264776 A1 | 10/2009 | Vardy |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0287467 A1* | 11/2009 | Sparks ............... A61B 34/10 607/116 |
| 2009/0314063 A1 | 12/2009 | Sternby |
| 2010/0004588 A1 | 1/2010 | Yeh |
| 2010/0010425 A1 | 1/2010 | Yu |
| 2010/0010429 A1 | 1/2010 | Childers |
| 2010/0042035 A1 | 2/2010 | Moissl |
| 2010/0061892 A1 | 3/2010 | Flaim |
| 2010/0076398 A1 | 3/2010 | Scheurer |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0113891 A1 | 5/2010 | Barrett |
| 2010/0114012 A1 | 5/2010 | Sandford |
| 2010/0137693 A1 | 6/2010 | Porras |
| 2010/0137782 A1 | 6/2010 | Jansson |
| 2010/0168546 A1 | 7/2010 | Kamath |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0264086 A1 | 10/2010 | Noack |
| 2010/0312172 A1 | 12/2010 | Hoffman |
| 2011/0017665 A1 | 1/2011 | Updyke |
| 2011/0048949 A1 | 3/2011 | Ding et al. |
| 2011/0066006 A1 | 3/2011 | Banet |
| 2011/0066043 A1 | 3/2011 | Banet |
| 2011/0071465 A1 | 3/2011 | Wang |
| 2011/0077574 A1 | 3/2011 | Sigg |
| 2011/0077575 A1 | 3/2011 | Kraemer |
| 2011/0079558 A1 | 4/2011 | Raimann |
| 2011/0081728 A1 | 4/2011 | Putnam |
| 2011/0087187 A1 | 4/2011 | Beck |
| 2011/0100909 A1 | 5/2011 | Stange |
| 2011/0106003 A1 | 5/2011 | Childers |
| 2011/0130666 A1 | 6/2011 | Dong |
| 2011/0137136 A1 | 6/2011 | Kotanko |
| 2011/0141116 A1 | 6/2011 | Dalesch |
| 2011/0144570 A1 | 6/2011 | Childers |
| 2011/0184340 A1 | 7/2011 | Tan |
| 2011/0208105 A1 | 8/2011 | Brandl |
| 2011/0272337 A1 | 11/2011 | Palmer |
| 2011/0301447 A1 | 12/2011 | Park |
| 2011/0301472 A1 | 12/2011 | Grober |
| 2012/0016228 A1 | 1/2012 | Kroh |
| 2012/0029937 A1 | 2/2012 | Neftel |
| 2012/0083729 A1 | 4/2012 | Childers |
| 2012/0085707 A1 | 4/2012 | Beiriger |
| 2012/0115248 A1 | 5/2012 | Ansyln |
| 2012/0135396 A1 | 5/2012 | McDevitt |
| 2012/0181230 A1 | 7/2012 | Kloeffel |
| 2012/0220528 A1 | 8/2012 | VanAntwerp |
| 2012/0258545 A1 | 10/2012 | Ash |
| 2012/0258546 A1 | 10/2012 | Marran |
| 2012/0259276 A1 | 10/2012 | Childers |
| 2012/0273354 A1 | 11/2012 | Soykan |

(56) References Cited

U.S. PATENT DOCUMENTS

| | | |
|---|---|---|
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0283581 A1 | 11/2012 | Olde et al. |
| 2012/0303079 A1 | 11/2012 | Mahajan |
| 2013/0037465 A1 | 2/2013 | Heyes |
| 2013/0062265 A1 | 3/2013 | Balschat |
| 2013/0116578 A1 | 5/2013 | QiAn |
| 2013/0168316 A1 | 7/2013 | Noguchi |
| 2013/0186759 A1 | 7/2013 | Lin |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228517 A1 | 9/2013 | Roger |
| 2013/0231607 A1 | 9/2013 | Roger |
| 2013/0248426 A1 | 9/2013 | Pouchoulin |
| 2013/0274642 A1 | 10/2013 | Soykan |
| 2013/0324915 A1 | 12/2013 | Britton |
| 2013/0330208 A1 | 12/2013 | Ly |
| 2013/0331774 A1 | 12/2013 | Farrell |
| 2014/0018727 A1 | 1/2014 | Burbank |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0216250 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2014/0276100 A1 | 9/2014 | Satterfield |
| 2014/0314625 A1 | 10/2014 | Clift |
| 2015/0032023 A1 | 1/2015 | Soykan |
| 2015/0080682 A1 | 3/2015 | Gerber |
| 2015/0088047 A1 | 3/2015 | Gerber |
| 2015/0144539 A1 | 5/2015 | Pudil |
| 2015/0148697 A1 | 5/2015 | Burnes |
| 2015/0149096 A1 | 5/2015 | Soykan |
| 2015/0250427 A1 | 9/2015 | Soykan |
| 2015/0343126 A1 | 12/2015 | Merchant |
| 2015/0352269 A1 | 12/2015 | Gerber |
| 2015/0367054 A1 | 12/2015 | Gerber |
| 2016/0023467 A1 | 2/2016 | Smith |
| 2016/0143774 A1 | 5/2016 | Burnett |
| 2016/0166753 A1 | 6/2016 | Meyer |
| 2016/0206801 A1 | 7/2016 | Gerber |
| 2016/0331884 A1 | 11/2016 | Sigg |
| 2017/0319768 A1 | 11/2017 | Szpara |
| 2017/0364660 A1* | 12/2017 | Vigersky ............ A61M 5/14244 |
| 2018/0043080 A1 | 2/2018 | Gerber |
| 2018/0221555 A1 | 8/2018 | Rohde |
| 2019/0125952 A1 | 5/2019 | Jansson |
| 2019/0125954 A1 | 5/2019 | Mathiot |
| 2019/0151526 A1 | 5/2019 | Wieslander |
| 2019/0240389 A1 | 8/2019 | Rohde |
| 2020/0019823 A1* | 1/2020 | Wang ...................... G16H 50/20 |
| 2020/0282218 A1* | 9/2020 | McDonald ......... A61N 1/37235 |
| 2022/0031947 A1* | 2/2022 | Onesti ................ A61M 5/1723 |
| 2022/0051773 A1* | 2/2022 | Appelbaum ........... G16H 10/40 |

FOREIGN PATENT DOCUMENTS

| | | | |
|---|---|---|---|
| CN | 101193667 | 6/2008 | |
| CN | 101300476 A | 11/2008 | |
| CN | 101400997 | 1/2009 | |
| CN | 101482572 | 7/2009 | |
| CN | 201342127 | 11/2009 | |
| CN | 101726465 | 6/2010 | |
| CN | 202048893 | 3/2011 | |
| CN | 103037917 | 4/2013 | |
| CN | 103180712 | 6/2013 | |
| CN | 103339503 | 10/2013 | |
| CN | 103394139 | 11/2013 | |
| CN | 103619372 | 3/2014 | |
| CN | 103751871 | 4/2014 | |
| CN | 103803479 | 5/2014 | |
| CN | 103901025 | 7/2014 | |
| CN | 104174077 | 12/2014 | |
| CN | 104685342 | 6/2015 | |
| CN | 104833635 A | 8/2015 | |
| CN | 105008893 B | 10/2015 | |
| CN | 105115921 | 12/2015 | |
| CN | 105142692 | 12/2015 | |
| CN | 105692957 A | 6/2016 | |
| CN | 105928939 | 7/2016 | |
| CN | 106124491 | 11/2016 | |
| CN | 205672288 | 11/2016 | |
| CN | 107206147 | 9/2017 | |
| CN | 110415831 A * | 11/2019 | ............. G16H 10/60 |
| CN | 101644667 | 2/2020 | |
| CN | 212619551 U * | 2/2021 | |
| DE | 3224823 | 1/1984 | |
| DE | 102006028172 A1 | 12/2017 | |
| EP | 0266795 A2 | 11/1987 | |
| EP | 0402505 | 12/1990 | |
| EP | 0272414 | 10/1991 | |
| EP | 0330892 | 7/1994 | |
| EP | 1175238 | 11/2000 | |
| EP | 1085295 | 11/2001 | |
| EP | 1281351 | 2/2003 | |
| EP | 2308526 | 10/2003 | |
| EP | 1364666 A1 | 11/2003 | |
| EP | 1523347 | 1/2004 | |
| EP | 1523350 | 1/2004 | |
| EP | 0906768 B1 | 2/2004 | |
| EP | 1691863 | 4/2005 | |
| EP | 2116269 | 2/2008 | |
| EP | 1450879 | 10/2008 | |
| EP | 1514562 | 4/2009 | |
| EP | 2219703 | 5/2009 | |
| EP | 1592494 B1 | 6/2009 | |
| EP | 2398529 | 11/2010 | |
| EP | 2575827 A2 | 12/2010 | |
| EP | 2100553 | 8/2011 | |
| EP | 2576453 A2 | 12/2011 | |
| EP | 2701580 | 11/2012 | |
| EP | 2701595 | 11/2012 | |
| EP | 1345856 B1 | 3/2013 | |
| EP | 2344220 B1 | 4/2013 | |
| EP | 1351756 | 7/2013 | |
| EP | 2190498 | 7/2013 | |
| EP | 2701596 | 3/2014 | |
| EP | 1582226 | 1/2016 | |
| JP | S55138462 | 10/1980 | |
| JP | S63-143077 | 11/1987 | |
| JP | 2002533170 | 10/2002 | |
| JP | 2002542900 | 12/2002 | |
| JP | 2003235965 | 8/2003 | |
| JP | 2005-533573 | 11/2005 | |
| JP | 5-99464 | 10/2012 | |
| KR | 20010109443 A * | 12/2001 | |
| WO | WO1992005814 | 4/1992 | |
| WO | 1995003839 | 2/1995 | |
| WO | WO 1998054563 | 12/1998 | |
| WO | WO1999006082 | 2/1999 | |
| WO | 9937342 | 7/1999 | |
| WO | PCT1124599 | 5/2000 | |
| WO | 0057935 | 10/2000 | |
| WO | WO2000057935 A1 | 10/2000 | |

(56) References Cited

FOREIGN PATENT DOCUMENTS

| | | |
|---|---|---|
| WO | 2000066197 | 11/2000 |
| WO | 200170307 A1 | 9/2001 |
| WO | 2001085295 A2 | 9/2001 |
| WO | 0185295 A2 | 11/2001 |
| WO | 2002013691 | 2/2002 |
| WO | WO 20020053211 | 7/2002 |
| WO | 2003043677 A2 | 5/2003 |
| WO | 2003043680 | 5/2003 |
| WO | 2003051422 A2 | 6/2003 |
| WO | 2004008826 | 1/2004 |
| WO | 2004009156 | 1/2004 |
| WO | 2004009158 | 1/2004 |
| WO | 2004030716 A2 | 4/2004 |
| WO | 2004030717 A2 | 4/2004 |
| WO | 2004064616 A2 | 8/2004 |
| WO | 2005033701 | 4/2005 |
| WO | 2005061026 | 7/2005 |
| WO | 2005123230 A2 | 12/2005 |
| WO | 2006011009 | 2/2006 |
| WO | 2006017446 | 2/2006 |
| WO | 2007038347 | 4/2007 |
| WO | 2007089855 A2 | 8/2007 |
| WO | 20070115321 | 10/2007 |
| WO | WO2009094035 A1 | 1/2008 |
| WO | 2008037410 | 4/2008 |
| WO | 2009026603 | 12/2008 |
| WO | 2009024566 | 2/2009 |
| WO | 2009026603 A1 | 3/2009 |
| WO | 2009061608 | 5/2009 |
| WO | 2009094184 | 7/2009 |
| WO | 2009157877 A1 | 12/2009 |
| WO | 2009157878 A1 | 12/2009 |
| WO | WO2009154955 A2 | 12/2009 |
| WO | WO 20090154955 | 12/2009 |
| WO | 2010024963 | 3/2010 |
| WO | 2010028860 | 3/2010 |
| WO | 2010033314 | 3/2010 |
| WO | 2010033699 | 3/2010 |
| WO | 2010077851 | 7/2010 |
| WO | 2010096659 | 10/2010 |
| WO | 2010121820 | 10/2010 |
| WO | 2011025705 A1 | 3/2011 |
| WO | 2011026645 | 3/2011 |
| WO | WO2013022760 A1 | 8/2011 |
| WO | WO 2011/132046 | 10/2011 |
| WO | 2011137693 | 11/2011 |
| WO | WO2011161056 | 12/2011 |
| WO | 2012042323 | 4/2012 |
| WO | 2012050781 | 4/2012 |
| WO | 2012051996 | 4/2012 |
| WO | 2012073420 | 7/2012 |
| WO | WO 2012/129501 | 9/2012 |
| WO | 2012148781 | 11/2012 |
| WO | 2012148784 | 11/2012 |
| WO | 2012148786 | 11/2012 |
| WO | 2012148787 A1 | 11/2012 |
| WO | 2012148789 | 11/2012 |
| WO | 2012162515 A2 | 11/2012 |
| WO | WO2012148788 A1 | 11/2012 |
| WO | WO 20120148784 | 11/2012 |
| WO | 2012172398 | 12/2012 |
| WO | 2013019179 A1 | 2/2013 |
| WO | 2013019994 A2 | 2/2013 |
| WO | 2013025844 | 2/2013 |
| WO | 2013028809 A3 | 2/2013 |
| WO | 2013101292 | 7/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A1 | 8/2013 |
| WO | 2013121162 A1 | 8/2013 |
| WO | 2013140346 | 9/2013 |
| WO | 2013141896 | 9/2013 |
| WO | 14066254 | 5/2014 |
| WO | 14066255 | 5/2014 |
| WO | 14077082 | 5/2014 |
| WO | 2014121162 | 8/2014 |
| WO | 2014121163 | 8/2014 |
| WO | 2014121167 | 8/2014 |
| WO | 2014121169 | 8/2014 |
| WO | WO2014121161 | 8/2014 |
| WO | WO 20140121161 | 8/2014 |
| WO | WO 20140121169 | 8/2014 |
| WO | WO2015081221 A1 | 6/2015 |
| WO | WO 20150130205 | 9/2015 |
| WO | WO 20150159280 | 10/2015 |
| WO | WO 20160080883 | 5/2016 |
| WO | WO 20170034452 | 3/2017 |
| WO | WO 2017/176687 | 10/2017 |

OTHER PUBLICATIONS

Henderson, et al, "Online Preparation of Sterile Pyrogen-Free Electrolyte Solution," Trans. Am. Soc. Artif. Intern.Organs, 1978 pp. 465-467.
Indian OA of Nov. 21, 2019 in 2981/KOLNP/2013.
Indian Office Action for Application 201714030219, dated May 31, 2021.
International Preliminary Report on Patentability for App. No. PCT/US2019/019334, dated Jun. 12, 2019.
Laurent, Jeanpierre, "Continuous Monitoring of Dynamic Systems: Application to Monitoring of Dialyzed Patients" Oct. 30, 2004, received from internet: http://laurent.jeanpierre1.free.fr/recherche/papiers/aista2004.pdf.
Office Action for Chinese Application No. 201710779349.3, dated Oct. 9, 2019.
Office Action for European App. No. 17190066.5, dated Mar. 7, 2019.
Office Action for European App. No. 17718241.7, dated Apr. 2, 2020.
Office Action in Chinese App. No. 201710778666.3 dated Sep. 19, 2019.
Office Action in Chinese App. No. 201780019238.0, dated Sep. 25, 2020.
PCT/US2016/058579 International Search Report dated Jan. 31, 2017.
PCT/US2016/058579 Written Opinion dated Jan. 31, 2017.
PCT/US2017/025868 International Search Report dated Jun. 29, 2017.
PCT/US2017/025868 Written Opinion dated Jun. 29, 2017.
PCT/US2017/030377 International Search Report dated Sep. 1, 2017.
PCT/US2017/030377 Written Opinion dated Sep. 1, 2017.
PCTUS20170146199 ISR and written opinion, Feb. 19, 2018.
PCTUS2017025858 International Search Report dated Jun. 29, 2017.
PCTUS2017025858 Written Opinion dated Jun. 29, 2017.
PCTUS2017025876 International Search Report dated Jun. 29, 2017.
PCTUS2017025876 Written Opinion dated Jun. 29, 2017.
Schmitt, et al, "Colorimetric Gas Sensing with Enhanced Sensitivity," Procedia Engineering, vol. 168, Sep. 3, 2016, pp. 1237-1240.
Second Chinese Office Action for Application No. 201811107614.4, dated Apr. 15, 2021.
Wollenstein, et al, "Colorimetric gas sensors for the detection of ammonia, nitrogen dioxide, and carbon monoxide: current status and research trends", Sensor and Test Conference 2011, Jan. 2, 2011, pp. 562-567.
Written Opinion in Dutch App. No. 2018577, dated Nov. 2, 2017.
Â€œ Resources, environment and sustainable development of agriculture,â€• edited by Liu Zhaopu, China Agricultural Science and Technology Press, pp. 209-211, Aug. 31, 1994.
Â€œ Rural Medical and Health Handbook, â€• written by Shanghai â€œRural Medical and Health Handbook Writing team, Shanghai Science and Technology Press, Jun. 1968, p. 435.

(56) References Cited

OTHER PUBLICATIONS

"Surface water environmental quality standard non-ionic ammonia conversion method," Teng Enjiang, et al, "China Environmental Monitoring," vol. 11, No. 4, pp. 7-9, Dec. 31, 1995.
Brynda, et al., The detection of toman 2-microglcbuiin by grating coupler immunosensor with three dimensional antibody networks. Biosensors & Bioelectronics, 1999, 363-368, 14(4).
Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
Zhong, et. al., Miniature urea sensor based on H(+)-ion sensitive field effect transistor and its application in clinical analysis, Chin. J. Biotechnol., 1992, 57-65. 8(1).
PCT/US2012/034331, International Search Report and Written Opinion dated Jul. 9, 2012.
Roberts M, The regenerative dialysis (REDY) sorbent system. Nephrology, 1998, 275-278:4.
Hemametrics, Crit-Line Hematocrit Accuracy, 2003, 1-5, vol. 1, Tech Note No. 11 (Rev. D).
Weissman, S., et al., Hydroxyurea-induced hepatitis in human immunodeficiency virus-positive patients. Clin. Infec. Dis, (Jul. 29, 1999): 223-224.
PCT/US2012/034334, International Search Report, Jul. 6, 2012.
PCT/US2012/034335, International Search Report, Sep. 5, 2012.
PCT/US/2012/034327, International Search Report, Aug. 13, 2013.
PCT/US/2012/034329, International Search Report, Dec. 3, 2012.
Foley, et al., Long Interdialytic Interval and Martality among Patients Receiving Hemodialysis, N Engl Jrnl Med. 2011:365(12):1099-1107.
PCT International Search Report from International Application No. PCT/US2014/067650, dated Mar. 9, 2015.
Wang, Fundamentals of intrathoracic impedance monitoring in heart failure, Am. J. Cardiology, 2007, 3G-10G: Suppl.
PCT/US2014/067650 International Search Report Written Opinion mailed Mar. 9, 2015.
Bleyer, et al., Kidney International. Jun. 2006; 69(12):2268-2273.
Bleyer, et. al., Sudden and cardiac death rated in hemodialysis patients, Kidney International. 1999, 1553-1559: 55.
PCT/US2012/034335, International Preliminary Report on Patentability, Oct. 29, 2013.
PCT/US2012/034303, Internationa Search Report, Jul. 6, 2013.
PCT/US2012/034332, Internatonal Preliminary Report on Patentability, Oct. 29, 2013.
PCT/US2012/034333, International Preliminary Report on Patentability, Oct. 29, 2013.
PCT/US2012/034333, International Search Report, Aug. 29, 2012.
PCT/US2012/034327, International Preliminary Report on Patentability, Oct. 29, 2013.
PCT/US2012/034330, International Preliminary Report on Patentability, Oct. 29, 2013.
Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
Redfield, et. al., Restoration of renal response to atria! natriuretic factor in experimental low-output heat failure, Am. J. Physiol., Oct. 1, 1989, R917-923:257.
Rogoza, et. al., Validation of A&D UA-767 device for the self-measurement of blood pressure, Blood Pressure Monitoring, 2000, 227-231, 5(4).
PCT/US2012/034329, International Preliminary Report on Patentability, Oct. 29, 2013.
Lima, et. al., An electrochemical sensor based on nanostructure hollandite-type manganese oxide for detection of potassium ion, Sensors, Aug. 24, 2009, 6613-8625, 9.
Maclean, et, al., Effects of hindlimb contraction on pressor and muscle interstitial metabolite responses in the cat, J. App. Physiol., 1998, 1583-1592, 85(4).
U.S. Appl. No. 13/757,693, dated Feb. 1, 2013.
PCT/US2014/014357 International Search Report and Written Opinion dated May 19, 2014.
PCT/US2014/014357 International Search Report and Written Opinion mailed May 19, 2014.
Ronco et al. 2008, Cardiorenal Syndrome, Journal American College Cardiology, 52:1527-1539, Abstract.
Overgaard, et. al., Activity-induced recovery of excitability in K+-depressed rat soleus muscle, Am. J. P 280: R48-R55, Jan. 1, 2001.
Overgaard et. al., Relations between excitability and contractility in rate soleusmuscle: role of the NA+-K+ pump and NA+-K-S gradients. Journal of Physiology, 1999, 215-225, 518(1).
Zoccali, Pulmonary Congestion Predicts Cardiac Events and Mortality in ESRD, Clinical Epidemiology, J. Am Soc Nephrol 24:639-646, 2013.
Coast, et al. 1990, An approach to Cardiac Arrhythmia analysis Using Hidden Markov Models, IEEE Transactions On Biomedical Engineering. 1990, 37(9):826-835.
Weiner, et al., Article: Cardiac Function and Cardiovascular Disease in Chronic Kidney Disease, Book: Primer on Kidney Diseases (Author: Greenberg, et al.), 2009,499-505, 5th Ed., Saunders Elsevier, Philadelphia, PA.
Velasco, Optimal Fluid Control can Normalize Cardiovascular Risk Markers and Limit Left Ventricular Hypertrophy in Thrice Weekly Dialysis Patients, Hemodialysis Intenational, 16:465-472, 2012.
Whitman, CKD and Sudden Cardiac Death: Epidemiology, Mechanisms, and Therapeutic Approaches, J Am Soc Nephrol, 23:1929-1939, 2012.
Hall, Hospitalization for Congestive Heart Failure: United States, 2000-2010, NCHS Data Brief, No. 108, Oct. 2012.
Albert, Fluid Management Strategies in Heart Failure, Critical Care Nurse, 32:20-32, 2012.
PCT/US2014/065201 International Search Report mailed May 26, 2015.
Genovesi, et al., Nephrology, Dialysis, Transplantation 2009; 24(8):2529-2536.
Secemsky, et. al., High prevalence of cardiac autonomic dysfunction and T-wave alternans in dialysis patients. Heart Rhythm, Apr. 2011, 592-598 : vol. 8, No. 4.
Gambro AK 96 Dialysis Machine Operators Manual, Dec. 2012. p. 1-140.
Gambro AK 96 Dialysis Machine Operators Manual, Dec. 2012. p. 141-280.
Gambro AK 96 Dialysis Machine Operators Manual, Dec. 2012. p. 281-420.
Gambro AK 96 Dialysis Machine Operators Manual, Dec. 2012. p. 421-534.
Wei, et. al., Fullerene-cryptand coated piezoelectric crystal urea sensor based on urease, Analytica Chimica Acta, 2001,77-85:437.
Leifer et al., A Study on the Temperature Variation of Rise Velocity for Large Clean Bubbles, J. Atmospheric & Oceanic Tech., vol. 17, pp. 1392-1402, Oct. 2000.
Talaia, Terminal Velocity of a Bubble Rise in a Liquid Column, World Acad. of Sci., Engineering & Tech., vol. 28, pp. 264-268, Published Jan. 1, 2007.
The FHN Trial Group. In-Center. Hemodialysis Six Times per Week versus Three Times per Week, New England Journal of Medicine, 2010 Abstract.
PCT/US2012/034332, International Search Report, Jul. 5, 2012.
Siegenthaler, et al., Pulmonary fluid status monitoring with intrathoracic impedance, Journal of Clinical Monitoring and Computing, 24:449-451, published Jan. 12, 2011.
John Wm Agar: Review: Understanding sorbent dialysis systems, Nephrology, vol. 15, No. 4, Jun. 1, 2010, pp. 406-411.
European Office Action in Application 12717020.7 dated Sep. 14, 2016.
Office Action in Chinese Application No. 201510511657.9 Dated Dec. 28, 2016.
Lakerveld et al, Primary prevention of diabetes mellitus type 2 and cardiovascular diseases using a cognitive behavior program aimed at lifestyle changes in people at risk: Design of a randomized controlled trial, 2008, BMC Endocrine Disorders, 8(6): 1-19.

(56) References Cited

OTHER PUBLICATIONS

Gordhandas et al, Real-Time Extraction and Analysis of Key Morphological Features in the Electrocardiogram, for Data Compression and Clinical Decision Support, 2004, Computational Physiology, pp. 15-18.
European Office Action in Application 12717020.7 dated Dec. 11, 2015.
PCT/US2012/034331 International Preliminary Report on Patentability and Written Opinion dated Oct. 29, 2013.
Office Action in Chinese Application No. 201280020932.1 Dated Jan. 7, 2015.
Office Action in Chinese Application No. 201280020932.1 Dated Apr. 3, 2015.
PCT/US2012/034330, International Search Report and Written Opinion dated Aug. 28, 2012.
Office Action in Chinese Application No. 201280020937.4 dated Mar. 22, 2016.
Office Action in Japanese Application No. 2014-508434 dated Nov. 16, 2015.
Office Action in Japanese Application No. 2014-508434 dated Dec. 8, 2014.
Office Action in Japanese Application No. 2014-508434 dated Nov. 4, 2016.
Office Action in European Application No. 12717019.9 dated Feb. 16, 2017.
Office Action in Chinese Application No. 201510511657.9 dated May 10, 2017.
PCT/US2014/065201 International Preliminary Report on Patentability mailed May 19, 2016.
Office Action in European Application No. EP 12717021.5 dated Feb. 3, 2017.
Office Action in Chinese Application No. 201510593695.3 dated Jul. 12, 2017.
Office Action in European Application No. EP 12719170.8 dated Jan. 14, 2015.
Office Action in Japanese Application No. JP 2014-508437 dated Dec. 8, 2014.
Nedelkov, et. al., Design of buffer exchange surfaces and sensor chips for biosensor chip mass spectrometry, Proteomics, 2002, 441-446, 2(4).
European Search Report App 14865374.4, Jun. 12, 2017.
European Search Report for Application No. 14865128.4 dated Jun. 20, 2017.
Green et al., Sudden Cardiac Death in Hemodialysis Patients: an In-Depth Review , Am J Kidney Dis 57(6)921:929; published Apr. 18, 2011.
Rajan et al. Generalized Feature Extraction for Time-Varying Autoregressive Models, IEEE Transacion Signal Processing vol. 44, No. 10; published Oct. 1, 1996.
AU Examiners Report for Application No. 2017246829, dated Jan. 9, 2021.
Australian Office Action for App. No. 2016349521, dated Aug. 31, 2020.
Castellanos, et al., Clinical Relevance of Intraperitoneal Pressure in Peritoneal Dialysis Patients, Perit Dial Int. Sep.-Oct. 2017;37(5):562-567. doi: 10.3747/pdi.2016.00267. Epub Jul. 11, 2017.
Chinese Office Action for App. No. 201710778666.3, dated Feb. 25, 2020.
Chinese Office Action for App. No. 201710778666.3, dated Jul. 15, 2020.
Chinese Office Action for App. No. 201710778666.3, dated Nov. 20, 2020.
Chinese Office Action for App. No. 201710779349.3, dated Jun. 1, 2020.
Chinese Office Action for App. No. 201710779964.4, dated Apr. 14, 2020.
Chinese Office Action for App. No. 201710779964.4, dated Aug. 26, 2020.
Chinese Office Action for App. No. 201780019237.6, dated Feb. 1, 2021.
Chinese Office Action for App. No. 201780019237.6, dated May 25, 2020.
Chinese Office Action for App. No. 201780019238.0, dated May 7, 2020.
Chinese Office Action for App. No. 201780019362.7, dated Jun. 2, 2020.
Chinese Office Action for App. No. 201810121459.5, dated Aug. 17, 2020.
Chinese Office Action for App. No. 201810121459.5, dated Mar. 19, 2020.
Chinese Office Action for App. No. 201811107614.4, dated Sep. 28, 2020.
Chinese Office Action for App. No. 201811155891.2, dated Oct. 10, 2020.
Chinese Office Action for App. No. 2019071601874110, dated Jul. 19, 2019.
Chinese Office Action in App. No. 201480059332.5, Dated Mar. 30, 2018.
Dejardin, et al, Intraperitoneal pressure in PD patients: relationship to intraperitoneal volume, body size and PD-related complications, Nephrol Dial Transplant. May 2007;22(5):1437-44.
European Office Action for App. No. 12719842.2, dated Jul. 15, 2020.
European Office Action for App. No. 14859115.9, dated Mar. 25, 2020.
European Office Action for App. No. 17190053.3, dated Sep. 18, 2019.
European Office Action for App. No. 17718246.6, dated Apr. 2, 2020.
European Office Action for App. No. 18204841.3, dated Aug. 20, 2020.
European Office Action for App. No. 19173852.5, dated Aug. 28, 2020.
European Search For App. No. 17190081.4, dated Feb. 5, 2021.
European Search Report for App. No. 17185636.2, Dated Mar. 27, 2018.
European Search Report for App. No. 14859115.9, dated Jan. 5, 2018.
European Search Report for App. No. 17185636.2 dated Jan. 10, 2018.
European Search Report for App. No. 17185638.8, dated Dec. 19, 2017.
European Search Report for App. No. 17185808.7, dated Jan. 2, 2018.
European Search Report for App. No. 17185810.3, dated Dec. 15, 2017.
European Search Report for App. No. 17190053.3, dated Jan. 2, 2018.
European Search Report for App. No. 17190066.5, dated Jan. 16, 2018.
European Search Report for App. No. 17190081.4, dated Sep. 16, 2019.
European Search Report for App. No. 17190084.8, dated Feb. 9, 2018.
F. Locatelli, et al: "Haemodialysis with on-line monitoring equipment: tools or toys?" Nephrology Dialysis Transplantation., vol. 20, No. 1, Jan. 1, 2005.

\* cited by examiner

ARTIFICIAL INTELLIGENCE ASSISTED HOME THERAPY SETTINGS FOR DIALYSIS

FIELD

Devices, systems, and methods are provided for providing artificial intelligence assisted home therapy settings for a medical apparatus. The devices, system, and methods are related to, though not exclusively, to a system and method of providing artificial intelligence assisted home therapy settings for dialysis.

BACKGROUND

Biomedical devices and other therapeutic apparatus improve human lives by providing therapeutic treatment, which may for example treat diseases or otherwise improve the functioning of the human body. Certain biomedical devices are entering home use but can require relatively complex or specific control settings. The control settings are needed for proper function and usefulness of a medical treatment such as for hemodialysis. For example, in-center hemodialysis is often administered and monitored by trained, in-center clinicians. However, a nephrologist may prescribe home treatment of hemodialysis to remove toxins such as urea from the blood. In setting up home hemodialysis, the patient and a primary care partner can be trained to perform dialysis safely, and to handle problems in the event of adverse conditions during the session. The in-center training might take several weeks to several months. Apart from training, the patient and caretaker can be provided with material relevant to the medication, safety measures, proper usage, sanitation, installation, and access to 24-hour support from care centers. However, the resulting cognitive load on the patient and caretaker can be large. Even after many hours of training, some patients and caretakers may be unable to properly comprehend and adjust control settings as may be required. Moreover, even trained clinicians in a clinical environment may be overwhelmed or fail to implement or recognize a problem. These issues could result in inconsistencies or sub-optimal outcomes in the dialysis adequacy and may pose health and safety risks to the patient.

The known systems and methods fail to provide a suitable home therapy system that assists and/or automates the process of setting control parameters. The known systems and methods fail to ameliorate a steep learning curve and cognitive load on home therapy systems and methods imposed upon caregivers and patients receiving home dialysis. The known systems and methods fail to suggest and/or automate treatment parameters such as the blood flow rate/ profiles with visual representation rates during hemodialysis delivery and blood return for home therapy.

Hence, there is a need for an electronic system that can advise patients during in-home treatments. There is a need for systems and methods that can automate or provide recommendations that can be implemented by a user whether in a clinical or home setting. There is a related need to provide analysis of patient records and other historical data to assist in setting parameters for a therapy. There is a further need for systems and methods for providing recommendations for blood flow rate and similar treatment parameters influencing a medical therapy such as dialysis. There is a need for a machine implemented system and method for recommending and/or setting parameters used in dialysis. There is a need for a system and method suitable for dialysis home therapy. There is a related need for recommending and automating a blood flow rate using a therapy or smart engine with artificial intelligence. The need relates to assisting patients, caregivers, clinicians, and doctors administering treatment themselves in a home or clinical setting. The need includes aiding medical professionals who are experienced, but who can benefit from the insights of a machine learning system and method. The need extends a network connected medical device that receive and send data. The need still further includes a medical device that can receive and send algorithms, recommendations, or instructions of any type.

SUMMARY OF THE INVENTION

The systems and methods can help reduce a steep learning curve and cognitive load of performing therapy whether in a clinical or home setting by any type of user. The system and method disclosed herein can help both nurses and patients who are participating in-home dialysis, and also can help physicians and others in-clinic who are desirous of electronic assistance in sorting through the large volume of records available.

The first aspect relates to a medical device. In any embodiment, the medical device can include: a therapeutic subsystem to deliver a medical therapy, including one or more sensors to monitor a biometric health factor; a user interface; a controller, including a processor and a memory; therapy software including instructions encoded within the memory to instruct the processor to receive a prescribed therapy, to receive a therapeutic setting recommendation, and to display the therapeutic setting recommendation to an operator via the user interface; a network interface, and instructions to receive, via the network interface, a prepared artificial intelligence (AI) model from a cloud service; and an AI circuit having execution hardware including at least one logic gate, and further including instructions to instruct the execution hardware to execute the prepared AI model to recommend a therapy setting for the therapeutic subsystem, wherein the circuit is incorporated into the prepared AI model data from the sensor.

In any embodiment, the execution hardware can include the processor.

In any embodiment, the device can be selected from an insulin pump, a continuous positive airway pressure machine, an external neural stimulator, an intravenous fluid device, and a dialysis machine.

In any embodiment, the device can be a dialysis machine.

In any embodiment, the prepared AI model can incorporate input selected from analytical data from laboratory testing, historical treatment parameters, patient access type, dialyzer type, therapy method, patient condition, fluid removal, dialyzer permeability, patient weight, dry weight, treatment time, and treatment goal.

In any embodiment, the therapy setting recommendation can include a blood flow rate recommendation.

In any embodiment, the therapy software instructions can further automatically select a recommended blood flow rate.

In any embodiment, the therapy software instructions can further detect a changed blood flow rate during therapy, and the AI circuit can further predict a recommendation according to the changed blood flow rate.

In any embodiment, the sensor can detect an adverse condition, and the AI circuit can recommend a blood flow rate according to the adverse condition.

In any embodiment, the adverse condition can include low patient blood pressure.

In any embodiment, the therapy software instructions can further save one or more blood flow rate profiles for a patient.

In any embodiment, the therapeutic setting recommendation can be selected from blood flow rate, sodium profile, and ultrafiltration rate profile.

In any embodiment, the user interface can include a control to request a therapeutic setting recommendation.

In any embodiment, the user interface can include one or more controls to automatically accept or reject recommended therapeutic settings.

In any embodiment, the therapy software instructions can further download the treatment parameters from a cloud service.

In any embodiment, the AI circuit can provide a high clearance prediction.

In any embodiment, the AI circuit can further concurrently provide a plurality of recommended therapeutic settings.

In any embodiment, the AI circuit can provide an AI model selected from the group consisting of linear regression, logistic regression, linear discriminant analysis, decision tree, naïve Bayes, k-nearest neighbors, learning vector quantization, support vector machine, random forest, neural network, convolutional neural network, and deep neural network.

In any embodiment, a system can be provided, including the medical device of any previous embodiment, and further including a cloud service, the cloud service including a hardware platform including a processor and a memory, and instructions encoded within the memory to instruct the processor to receive a plurality of historical patient inputs and build the prepared model from the plurality of historical patient inputs.

In any embodiment, a system can be provided, wherein the prepared model can be a patient-specific model.

In any embodiment, a system can be provided, wherein the prepared model can be specific to a class of patients.

The features disclosed as being part of the first aspect can be in the first aspect, either alone or in combination, or follow any arrangement or permutation of any one or more of the described elements. Similarly, any features disclosed as being part of the first aspect can be in a second or third aspect described below, either alone or in combination, or follow any arrangement or permutation of any one or more of the described elements.

The second aspect relates to a method of providing therapy recommendations for a medical device. In any embodiment, the method can include: receiving a prescribed therapy regimen for a patient; receiving a patient profile for the patient; operating an artificial neural network (ANN) to compute a recommended therapy setting according to a regression model, wherein the prescribed therapy regimen and the patient profile are inputs to the regression model; and displaying the recommended therapy in a human-readable format.

In any embodiment, the method can further include executing on hardware that includes a processor.

In any embodiment, the device can be selected from an insulin pump, a continuous positive airway pressure machine, an external neural stimulator, an intravenous fluid device, and a dialysis machine.

In any embodiment, the device can be a dialysis machine.

In any embodiment, the ANN can receive an input selected from analytical data from laboratory testing, historical treatment parameters, patient access type, dialyzer type, therapy method, patient condition, fluid removal, dialyzer permeability, patient weight, dry weight, treatment time, and treatment goal.

In any embodiment, the recommended therapy setting can include a blood flow rate recommendation.

In any embodiment, the method can further include automatically selecting a recommended blood flow rate.

In any embodiment, the method can further include detecting a changed blood flow rate during therapy, and the ANN can further predict a recommendation according to the changed blood flow rate.

In any embodiment, the method can further include detecting an adverse condition, and the ANN can recommend a blood flow rate according to the adverse condition.

In any embodiment, the adverse condition can include low patient blood pressure.

In any embodiment, the method can further include saving one or more blood flow rate profiles for a patient.

In any embodiment, the method can further include selecting the recommended therapy setting from blood flow rate, sodium profile, and ultrafiltration rate profile.

In any embodiment, the method can further include requesting a therapeutic setting recommendation.

In any embodiment, the method can further include automatically accepting or rejecting recommended therapeutic settings.

In any embodiment, the method can further include downloading the historical treatment parameters from a cloud service.

In any embodiment, the ANN can provide a high clearance prediction.

In any embodiment, the ANN can further concurrently provide a plurality of recommended therapeutic settings.

The features disclosed as being part of the second aspect can be in the second aspect, either alone or in combination, or follow any arrangement or permutation of any one or more of the described elements. Similarly, any features disclosed as being part of the second aspect can be in the first or third aspect described below, either alone or in combination, or follow any arrangement or permutation of any one or more of the described elements.

The third aspect relates to one or more tangible, non-transitory computer-readable media. In any embodiment, the computer-readable media can have stored thereon executable instructions to: receive a therapy prescription for a patient; receive a patient profile for the patient; run, in an ANN, a regression model having as inputs the therapy prescription and the patient profile, and as an output a recommended therapy setting for a medical device; and operate a user interface to display the recommended therapy setting.

In any embodiment, the instructions can be to run on hardware including a processor.

In any embodiment, the instructions can be to operate a device selected from an insulin pump, a continuous positive airway pressure machine, an external neural stimulator, an intravenous fluid device, and a dialysis machine.

In any embodiment, the instructions can be to operate a dialysis machine.

In any embodiment, the ANN can receive an input selected from analytical data from laboratory testing, historical treatment parameters, patient access type, dialyzer type, therapy method, patient condition, fluid removal, dialyzer permeability, patient weight, dry weight, treatment time, and treatment goal.

In any embodiment, the recommended therapy setting can include a blood flow rate recommendation.

In any embodiment, the instructions can automatically select a recommended blood flow rate.

In any embodiment, the instructions can be to further detect a changed blood flow rate during therapy, and the ANN can further predict a recommendation according to the changed blood flow rate.

In any embodiment, the instructions can be to further detect an adverse condition, and the ANN can recommend a blood flow rate according to the adverse condition.

In any embodiment, the adverse condition can include low patient blood pressure.

In any embodiment, the instructions can be to further save one or more blood flow rate profiles for a patient.

In any embodiment, the recommended therapy setting can be selected from blood flow rate, sodium profile, and ultrafiltration rate profile.

In any embodiment, the user interface can include a control to request a therapeutic setting recommendation.

In any embodiment, the user interface can include one or more controls to automatically accept or reject recommended therapeutic settings.

In any embodiment, the instructions can be further to download the historical treatment parameters from a cloud service.

In any embodiment, the ANN can provide a high clearance prediction.

In any embodiment, the ANN can further concurrently provide a plurality of recommended therapeutic settings.

The features disclosed as being part of the third aspect can be in the third aspect, either alone or in combination, or follow any arrangement or permutation of any one or more of the described elements. Similarly, any features disclosed as being part of the third aspect can be in the first or second aspect, either alone or in combination, or follow any arrangement or permutation of any one or more of the described elements.

DETAILED DESCRIPTION

Figure 1:
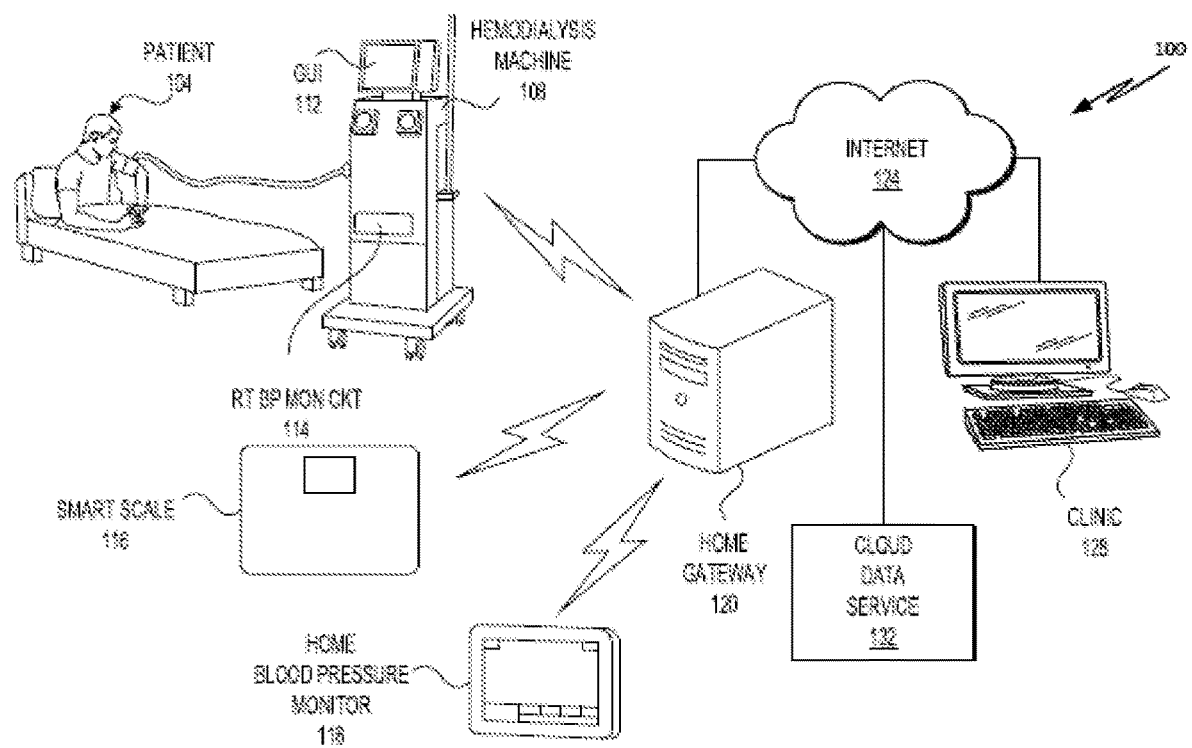
FIG. 1 is a system-level view of a medical device ecosystem.

Unless defined otherwise, all technical and scientific terms used have the same meaning as commonly understood by one of ordinary skill in the art.

The articles "a" and "an" are used to refer to one to over one (i.e., to at least one) of the grammatical object of the article. For example, "an element" means one element or over one element.

The term "biomedical device" refers to any device that provides therapy, monitoring, or telemetry for a biological entity, and most particularly, for a human. Biomedical devices can passively monitor a human patient, or they can actively administer a therapeutic service.

The term "biometric s" can be any measurement obtained from a living organism. In general, the measurement is indicative of a health status of the living organism such as analytical data obtained from various lab testing and history data or from any sensor that can sense a measurand of any type, e.g., blood pressure, body weight, temperature, etc. One of ordinary skill will appreciate that many biometric parameters can be indicated of a health status and are all contemplated.

The term "blood flow rate" refers to the rate at which blood is extracted and filtered during hemodialysis.

The term "blood flow rate profile" refers to a time series profile that defines blood flow rates at different points of therapy.

The term "blood pressure" refers to a measure of the systolic and diastolic blood pressure.

The term "circuit" refers to any electronic analog, digital, or mixed-signal electronic network. In the case of digital or mixed-signal networks, the circuit can also include instructions or other inputs that are used to program the circuit.

The term "cloud service" refers to any collection of one or more machines, connected via a network such as the internet, that provides a non-local service.

The term "continuous positive airway pressure machine" refers to a medical device that provides forced air to a patient while sleeping to mitigate sleep apnea.

The term "controller" refers to a programmable circuit, which can include instructions to program the circuit, that controls a device.

The term "convolutional neural network" refers to a form of neural network that uses mathematical convolution to define the relationship between neurons.

The term "decision tree" refers to a branching model, with yes/no (or similar) decisions at each branch.

The term "deep neural network" refers to a neural network that generally includes an input layer, one or more intermediate hidden layers, and an output layer, in which each neuron of each layer is linked to each neuron of the next layer.

The term "dialysis machine" refers to a medical device that provides in-home or in-clinic hemodialysis.

The term "dialyzer permeability" refers to the permeability of a hollow fiber dialyzer bundle.

The term "dialyzer type" refers to one of several types of dialyzers, such as coil, parallel plate, hollow fiber, or ultrafiltration.

The term "execution hardware" refers to programmable hardware to read and act on the instructions of a computer program.

The term "external neural stimulator" refers to an electrical device to stimulate neurons.

The term "high clearance prediction" refers to a predicted condition to provide high dialysis clearance.

The term "human-readable format" refers to any format that is readily perceptible and understandable by a human.

The term "instructions" refers to machine-readable data that cause a processor to execute an algorithm. In the case of a microprocessor or microcontroller, the instructions can be a series of operation codes that, in a particular sequence, cause the processor to execute a desired algorithm. In the case of a field-programmable gate array (FPGA) or application-specific integrated circuit (ASIC), the instructions can be written in a hardware description language that is used to configure the circuit to carry out the algorithm.

The term "insulin pump" refers to a medical device that injects insulin into a patient.

The term "interface" refers to any combination of hardware, software, and/or firmware that enables one object to communicatively couple to another object.

The term "intravenous fluid device" refers to a device that injects fluid into a vein.

The term "k-nearest neighbors" refers to a model that makes predictions by mapping an input data set into an n-dimensional space, and identifying, for each node of interest, the k nodes that are nearest to a point in the space.

The term "learning vector quantization" refers to an evolution of k-nearest neighbors that employs a neural network.

The term "linear discriminant analysis" refers to a subclass of logistic regression that can be used when two or more classes can exist in the output.

The term "linear regression" refers to a statistical model that fits data to a line.

The term "logic gate" refers to an electronic circuit that receives one or more logical inputs, and provides at least one logical output as a function such as AND, OR, XOR, NAND, NOR, XNOR, delay, unity, or selection.

The term "logistic regression" refers to a statistical model that fits data to a logarithm, and is able to predict binary results.

The term "medical device" refers to an electronic device that provides at least one medical function.

The term "memory" refers to any electronic medium capable of storing encoded data.

The term "naïve Bayes" refers to a model that can predict a conditional probability according to a Bayesian calculation.

The term "neural network" refers to a form of artificial intelligence, not limited to a single algorithm, in which artificial "neurons" are connected in a network.

The term "operator" refers to a human who operates a device.

The term "patient access type" refers to the type of access to the patient, commonly one of fistula, graft, or catheter.

The term "patient condition" refers to any measure of patient health or status.

The term "patient profile" refers to a profile of blood flow rate across time, specific to a patient.

The term "processor" refers to any programmable or configurable logic circuit, which can be configured to execute a desired algorithm. A processor can provide a generalized instruction set, such as in the case of a microprocessor or microcontroller or can be configured in hardware as in the case of an application-specific integrated circuit (FPGA). In some cases, processors can be emulated and/or virtualized. For example, virtualization technology can provide a virtual processor running under a hypervisor, or other kind of virtualization layer, in which case the "processor" can include the emulation layer, as well as the physical processor that ultimately executes the instructions.

The term "random decision forest" refers to a form of decision tree, where multiple samples are processed by decision trees, and the results are aggregated.

The term "sodium profile" refers to the sodium concentration of dialysis fluid.

The term "software" refers to any sequence of instructions to instruct a programmable hardware to carry out an algorithm.

The term "support vector machine" refers to a model that employs a hyperplane line that separates data input nodes with different values.

The term "therapeutic subsystem" refers to a portion of a medical apparatus that administers therapy or treatment to a patient.

The term "therapy" refers to a medical procedure or regimen delivered to a patient.

The term "therapy method" refers to the method by which a therapy is delivered to the patient.

The term "therapy regimen" refers to the prescribed parameters, length, and methods of a treatment.

The term "therapy software" refers to software that controls administration and/or monitoring of therapy.

The term "ultrafiltration" refers to a form of hemodialysis in which excess fluid, such as water, is removed from the blood (in addition to removing toxins).

The term "ultrafiltration rate profile" refers to a profile, over time, of the rate at which ultrafiltration is performed during hemodialysis.

Medical Device Ecosystem

FIG. 1 is a system-level view of a medical device ecosystem 100. Ecosystem 100 includes a home health network, wherein a treatment such as dialysis can be administered by patient 104, or by a caregiver for patient 104. The patient 104 can be connected to an immediate or easy access to a healthcare professional to monitor or adjust certain treatment parameters. The term "biometric health factor" can be any measurement obtained from a living organism. In general, the measurement is indicative of a health status of the living organism such as analytical data obtained from various lab testing and history data of treatment parameters such as patient access type, dialyzer type, therapy method, patient conditions, fluid removal, dialyzer permeability, patient's weight, dry weight, treatment time, treatment goal, and other physiological or appropriate clinical parameters to identify and recommend the optimal blood flow rate for a patient at each phase of hemodialysis treatment delivery.

Patient 104 operates hemodialysis machine 108, which includes a graphical user interface (GUI) 112. GUI 112 permits patient 104 to interact with hemodialysis machine 108, and to provide inputs and view outputs. For example, GUI 112 can include a flow rate profile display, which could optionally include flow rate points. In some cases, GUI 112 can include a touch-sensitive display, so that patient 104 can directly interact with GUI 112, via the display.

Hemodialysis machine 108 can include various sensors that provide feedback to monitor the success and safety of the dialysis operation. For example, a real-time blood pressure monitoring circuit (RT BP Mon.) 114 can be provided, so that the patient's blood pressure can be monitored in real-time, or near real-time, and so that the system can detect whether the patient's blood pressure drops dangerously low.

Ecosystem 100 can also include a home gateway 120, which connects to various devices that can help provide useful inputs to hemodialysis machine 108. For example, a smart scale 116 could be used to measure the patient's dry weight, and/or the patient's weight after dialysis. Home blood pressure monitor 118 could be used to periodically check the blood pressure of patient 104, and to keep track of blood pressure trends. In some illustrative embodiments, hemodialysis machine 108, smart scale 116, and/or home blood pressure monitor 118 can communicatively couple to home gateway 120, such as via a wired or wireless network. Home gateway 120 can act as a gateway between the home environment and internet 124, which provides a wider and uncontrolled network.

The home gateway 120 can provide for communication between the home gateway 120 and a cloud data service 132. The cloud data service 132 can have various software modules to connect to the home gateway 120. Notably, the cloud data service 132 can establish a data communication channel with the home gateway 120 through a TCP/IP protocol or other suitable process, where a terminal is connected to the home gateway 120. The home gateway 120 software can send a first software message to the cloud data service 132 through the data communication channel so that the home gateway 120 establishes connection with cloud data service 132. One of ordinary will understand that other suitable connection methods, steps, and protocols can be implemented to establish such connection with an external cloud server. The cloud data service 132 can communicatively couple to home gateway 120 via internet 124 and can provide services to patient 104. For example, cloud data service 132 can provide a pre-trained AI model to hemodialysis machine 108, which can enable an artificial intelligence circuit on hemodialysis machine 108 to provide treatment parameter suggestions, such as a suggested flow rate or a flow rate profile. In some cases, clinic 128 can also connect to cloud data service 132 via internet 124, or via an intranet or other internal network. Clinic 128 can provide data such as electronic health records, a treatment prescription, and other inputs as described herein to cloud data service 132. Cloud data service 132 can then use those data to build the pre-trained AI model for use by hemodialysis machine 108. In some cases, the pre-trained AI model can be specific to patient 104, rather than a general model that can be used by many patients. In other embodiments, a general model that is applicable to a class or group of patients could also be provided.

Medical Treatment Ecosystem

Figure 2:
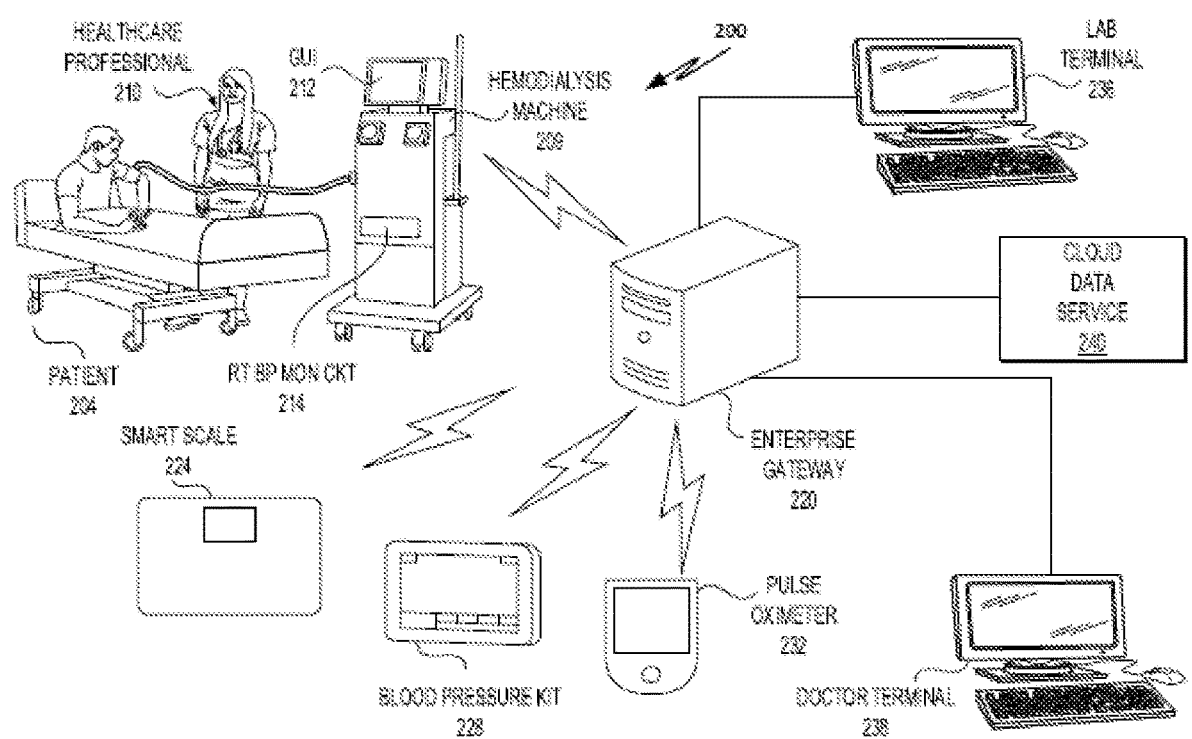
FIG. 2 is a system-level diagram of a medical treatment ecosystem.

FIG. 2 is a system-level diagram of a medical treatment ecosystem 200. Whereas medical device ecosystem 100 of FIG. 1 takes place in a home treatment context, ecosystem 200 can take place in a clinical setting. Thus, patient 204 can be assisted by a healthcare professional 210, who can be, for example, a registered nurse trained in the use of hemodialysis machine 209, or can be or include a nephrologist, or other healthcare professional. Healthcare professional 210 may, as a general rule, have greater training than patient 204, if patient 204 were required to operate hemodialysis machine 209 individually. However, healthcare professional 210 can still benefit from recommendations, such as a recommended blood flow rate or blood flow rate profile.

In this example, within the clinic there is an enterprise gateway 220, which provides connectivity between various devices. Similar to FIG. 1, enterprise gateway 220 connects either via an intranet or via the internet to cloud data service 240. Enterprise gateway 220 can also provide connections to a lab terminal 236 and a doctor terminal 238. A physician can use doctor terminal 238 to input parameters, such as a treatment prescription and other recommendations. Lab terminal 236 can provide lab results, as well as access to electronic health record (EHR) and other data. Cloud data service 240 can be configured to collect various inputs, and to build a pre-trained AI model that can be run on hemodialysis machine 209. Other inputs can be collected via smart devices around the clinic, such as a smart scale 224, a blood pressure kit 228, and a pulse oximeter 232, by way of illustrative and nonlimiting example. As before, these devices, along with hemodialysis machine 209, can communicatively couple to enterprise gateway 220 via a wired or wireless network. Thus, while healthcare professional 210 is administering treatment to patient 204 via hemodialysis machine 209, she can operate GUI 212 to select treatment options, including a blood flow rate. She can also have access to a button, such as a "quick assist" button, that provides the ability to request a recommendation for a blood flow rate, according to current treatment parameters. As before, a real-time or near real-time blood pressure monitoring circuit 214 can be provided on hemodialysis machine 209 and can monitor patient 204 to ensure that his blood pressure does not drop below a danger threshold.

Medical Device

Figure 3:
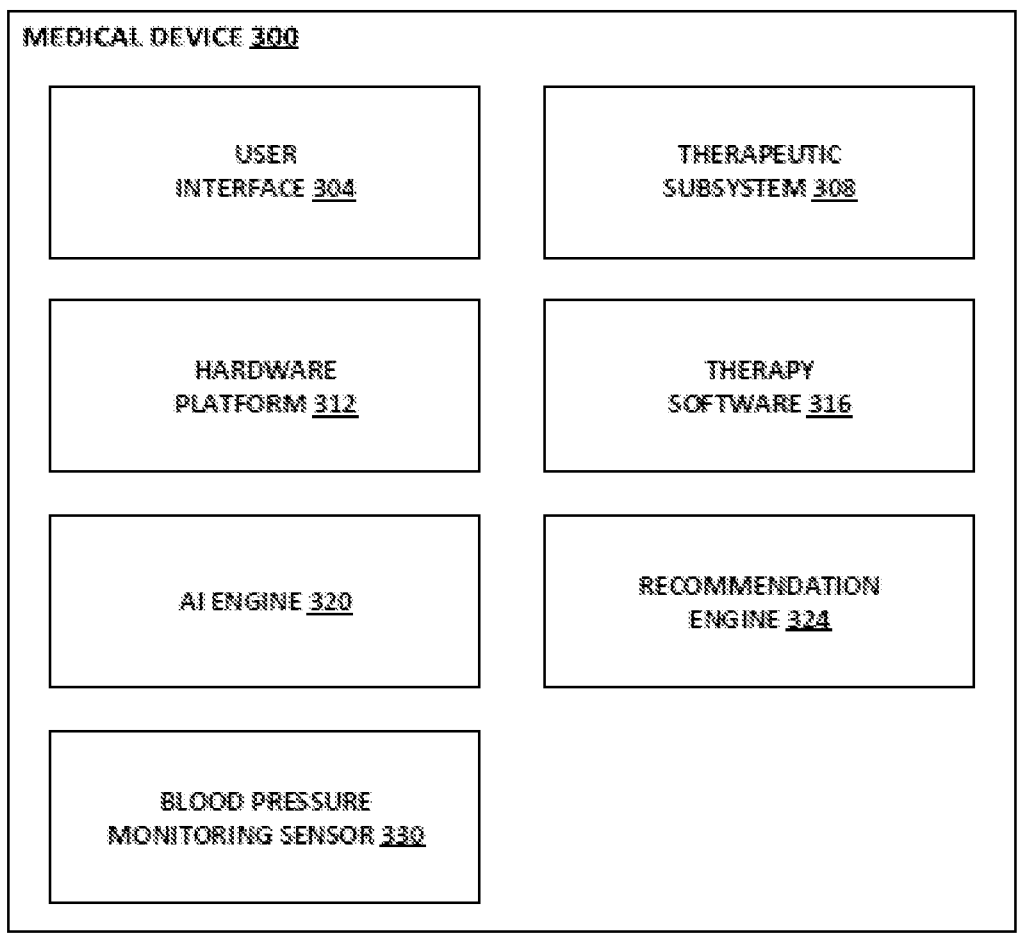
FIG. 3 is a block diagram of a medical device.

FIG. 3 is a block diagram of a medical device 300. Medical device 300 can be, for example, a hemodialysis machine, or any other suitable medical device. Furthermore, medical device 300 could also stand for a class of devices that could benefit from the teachings of the present specification, including devices that are not medical devices.

Medical device 300 includes a user interface 304, a therapeutic subsystem 308, a hardware platform 312, therapy software 316, an AI engine 320, and a recommendation engine 324. These are provided by way of illustrative and nonlimiting example. One of ordinary will understand that not all elements need be present in each embodiment, and some embodiments can include other elements. Furthermore, while these elements are shown as separate blocks, this does not necessarily imply that they are required to be provided as physically separate devices, or on separate hardware. The recommendation engine 324 can be provided may be a server, cloud service, or the like.

User interface 304 can include, for example, a touch-screen display, and can provide input options for configuring therapy. User interface 304 can also provide, for example, a graphical display of a blood flow rate or blood flow rate profile, as illustrated below in FIGS. 4 and 5.

Therapeutic subsystem 308 includes the hardware and software for providing the actual therapy. For example, therapeutic subsystem 308 can provide the pumps, filters, chemicals, pharmaceutical compounds, or other objects that are used to provide the therapy to the patient.

Hardware platform 312 can include the hardware for operating medical device 300. This could include, for example, a microcontroller, volatile and/or nonvolatile memory, interfaces, and other hardware elements. Hardware platform 312 can drive user interface 304, can control or interface with therapeutic subsystem 308, and can provide the platform for therapy software 316, AI engine 320, and recommendation engine 324.

Therapy software 316 can include software that interfaces with therapeutic subsystem 308 to provide therapy, to interface with sensors and other inputs, to collect user inputs via user interface 304, and to process results.

AI engine 320 includes an AI circuit which can be programmed to provide an artificial intelligence model. For example, AI engine 320 could include an ANN, a decision tree, or any other artificial intelligence engine or algorithm. By way of illustrative and nonlimiting example, AI engine 320 can provide an algorithm selected from a group including linear regression, logistic regression, linear discriminant analysis, decision tree, naïve Bayes, k-nearest neighbors, learning vector quantization, support vector machine, random forest, or deep neural network.

AI engine 320 may, in some examples, be a relatively limited AI circuit, and cannot provide all of the training or preprocessing that a full AI solution requires. Rather, AI engine 320 can receive a preprocessed or pre-trained model from an outside source, such as a cloud service, and can run that model based on localized inputs within medical device 300. Thus, much of the preprocessing can be provided in the cloud, where greater processing resources can be available. AI engine 320 can therefore be a relatively lightweight AI engine, and can perform only the processing necessary to make decisions in real-time, or near real-time, on medical device 300.

Recommendation engine 324 interfaces with user interface 304 and AI engine 320. Recommendation engine 324 can receive, via user interface 304, a request for a recommendation, such as when the user operates a quick assist button, or some other function. Recommendation engine 324 can also receive from AI engine 320 a recommendation, such as a recommended blood flow rate or blood flow rate profile. This can be provided to the user via user interface 304, and, in some embodiments, the user can be able to either accept or reject the recommendation.

Blood pressure monitoring sensor 330 can be used to monitor the patient's blood pressure in real-time, or near real-time, and to optionally compare that blood pressure to a threshold, to determine whether the patient's blood pressure is below a threshold with a safety margin, and/or below a danger threshold.

Thus, while there is an adequate knowledge base of individuals who understand hemodialysis therapy, and who have the experience to appropriately adjust parameters during sessions, the application and transition of this acquired knowledge can be a challenge. During in-center sessions, if there is a need to change programming parameters, an in-house nephrologist or experienced home therapy nurse can be consulted. But for the in-home care setting, the patient or caretaker may not even realize that a particular parameter requires a need to consult a professional. Thus, although 24-hour service support is available to put the patient in contact with a home therapy registered nurse (RN) or nephrologist, the patient may not even realize when these services are needed. Furthermore, even when the patient does realize that a consultation is required, the consultation can take a long time, requiring the patient to contact the 24-hour service, explain the issue, get potential solutions, and walk through the results.

Furthermore, for a nephrologist or RN to provide appropriate consultation, the professional may need to skim through the history of medical practice and EHRs for the patient to provide a prescription that is targeted to the patient's individual circumstances. The prescription may vary based on the experience level of the professional, as the professional may lack a generic tool to view treatment parameter recommendations.

Embodiments of this specification achieve benefits by suggesting and/or automating treatment parameters such as blood flow rate and profiles, and can optionally provide a visual representation of the blood flow rate during hemodialysis. This can be observed by both patients and attending nurses during hemodialysis delivery and blood return.

For many individuals, the effectiveness of dialysis treatment is dependent on the blood flow. Thus, the present specification uses a blood flow rate recommendation for dialysis treatment as an illustrative example of the principles taught herein. One of skill will understand that the dialysis machines disclosed herein could be replaced by any other biomedical device, or by any other device that could benefit from the teachings of this specification. Furthermore, blood flow rate could be replaced by any other treatment parameter that influences dialysis clearance, or by some other therapeutic factor for dialysis, or a different therapy. Furthermore, examples of the present specification are disclosed in terms of hemodialysis home therapy methods that are performed by patients or attended by registered nurses in the home. However, the teachings of this specification can also benefit physicians or other professionals who desire an aid for their own analysis. Embodiments disclosed herein recommend and automate blood flow rate using a therapy or smart engine with an AI assistance.

In one illustrative example, a cloud-based analysis module performs initial analysis on a number of parameters, and then provides a pre-trained AI model that can be deployed on an individual system. This pre-trained model can then be distributed, for example, via a secure network connection to an individual device that is performing in-home treatment. The individual device receives the pre-trained AI model, and runs the model in its own AI circuit. During treatment, the user can request a recommendation, such as a recommended blood flow profile, or the system can detect that the blood flow has an issue. For example, the blood flow rate can be too low to provide the desired therapy results, or a blood pressure sensor could indicate that the patient's blood pressure has dropped below a threshold, and thus, the blood flow rate should be decreased for the patient's health and safety.

Advantageously, by dividing the logic between two devices, the "heavy lifting" of the computations, such as parsing large volumes of data and training a model, can be performed on the backend in the cloud, where more processing power can be available. On the front end, at the dialysis machine, the pre-trained model can be run on the AI circuit, utilizing relatively fewer system resources. Although this split between workloads is illustrated as an example in this specification, one of skill will understand that any of the examples shown below, including the examples that explicitly show such a split, could also be applied to a system where all the processing occurs on a single device.

The analytical system disclosed herein uses a combination of analytical data obtained from various lab testing and history data for treatment parameters to identify and recommend a suggested blood flow rate for a patient, which can be delivered at each phase of a hemodialysis treatment delivery. Treatment parameters can include, by way of illustrative and nonlimiting example, patient access type, dialyzer type, therapy method, patient conditions, fluid removal, dialyzer permeability, patient weight, patient dry weight (e.g., a patient's weight before treatment), treatment time, treatment goals, or others. The system disclosed can provide multiple treatment parameter profile suggestions. This can allow the user to choose between a number of recommended ranges.

Furthermore, the system can suggest a recommended blood flow rate in the event of an adverse common condition during the treatment session. The patient or nurse can choose to accept or override a recommendation. For example, an adverse condition could include an unsafe drop in blood pressure. In that case, the system can suggest a change to the treatment parameters, such as the blood flow rate. The user can choose to accept or reject this recommendation, although in some embodiments, if the blood pressure or other parameter drops below an important threshold, the user selection can be overridden to protect the patient's life, health, or safety.

In at least some embodiments, the system suggests or automates the blood flow rate settings upon a user consensus, and/or in the event of adverse conditions, such as for low patient blood pressure. The system can also suggest or automate blood flow rates for common conditions that require changes in blood flow rate during hemodialysis delivery and blood return. In some cases, if the blood flow rate is changed (i.e., increased or decreased) during the treatment session, the system can dynamically predict a recommendation based on the changed blood flow rate, and provide that recommendation in real-time, or near real-time.

In further embodiments, the system can save the recommended blood flow rate profiles for a patient on the hemodialysis machine, or on a patient access card that is used to access and control the hemodialysis machine. This can include saving blood flow rate profiles for a home hemodialysis patient, or for in-clinic hemodialysis use.

Notably, although blood flow rate has been illustrated herein as an example parameter, the system can also be used to adjust other parameters, such as sodium profiles, ultrafiltration rate profiles, and other profiles that can influence dialysis adequacy.

may be surprised to learn that the reading material and the training do not translate directly into handling real-world issues during real treatment sessions. Issues could range from incorrect consumable installation, incorrect treatment parameter programming, incorrect medication, obstruction in the extracorporeal blood tube, incorrect handling of pressure alarms, and errors in treatment delivery.

Smart Therapy Analysis Module

As discussed above, a smart therapy analysis module is a software module that optionally can be hosted in the cloud. The smart therapy analysis module can be used to pre-train an AI model that can be executed on the home dialysis machine. This software can be provided with inputs that include analytical data. The analytical data can be obtained by lab regression testing of various treatment parameters, physiological parameters, adverse condition combinations, and the resultant clinical output. The treatment parameters could include, by way of illustrative and nonlimiting example, prescribed blood flow rate, treatment time, treatment goal, fluid to be removed, patient conditions, dialyzer type used, vascular access type, patient age, patient gender, patient physiological condition, patient treatment logs, or others. The clinical output data might include urea removed ratio/percentage and Kt/V over a time period.

The smart therapy software module can be used to analyze these factors, and provide a pre-trained AI model, or other inputs that can be used to control an AI model, which can be executed on the home therapy machine.

Artificial Intelligence Module

The home dialysis machine can include an AI module. The input for the AI module can include the data analytics from the smart therapy analysis module discussed above, which can be retrieved via a secure internet connection. Other inputs can include current treatment parameters entered on the user interface (UI), or parameters obtained in a safe and encrypted form from a cloud-based EHR repository. The AI circuit can compare the smart therapy and the current EHR data to provide a recommended high clearance prediction, and a recommended range of treatment parameters. The predictions and recommendations can be gathered using a basic machine learning regression model, or some other machine learning model. The regression model can identify patterns, relationships between different combinations of data, or other relationships. During a new treatment session, the model can suggest appropriate treatment parameters for high clearance and overall clinical output of the session. In some cases, current EHR details entered on the UI can be compared to lab result data analytics, to provide important treatment parameter adjustments for higher clearance.

The patient's blood sample may be measured to determine whether the dialysis has removed enough waste product from the blood. The patient's blood sample may be measured for dialysis adequacy periodically, including before dialysis starts, a month after dialysis is started, or twice a month during dialysis, by way of nonlimiting example. Factors that may be computed from these measurements include a urea reduction ratio (URR), and a clearance per treatment over water volume t. These are calculated from the patient's blood sample to assess the dialysis adequacy. Based on these values, a physician may update the treatment parameters to improve dialysis adequacy. To improve dialysis clearance K, the physician may attempt to optimize the rate at which blood flows through the dialyzer, referred to as the "blood flow rate." If the blood flow is optimal, then the dialysis clearance rate is improved. However, the blood flow rate cannot be increased indiscriminately. Changing the blood flow rate may depend on factors including the maturity and strength of the patient's vascular access. The clearance may be adjusted by choosing the correct treatment parameters, such as dialyzer type, treatment time, treatment goal, patient's weight, patient conditions, and similar. Blood flow rate is a primary treatment parameter for the dialysis efficiency and efficacy. Fluctuations in the blood flow rate during the dialysis influence the dialysis clearance and the health of vascular access.

In some cases, in-center treatments are performed on average three times per week, usually for about four hours per session. Home hemodialysis may also be performed, depending on the type of therapy chosen. Long home therapy sessions may be performed three times a week (e.g., for four hours). Short treatments may be done five to six days a week, with shorter treatment times between three and four hours. Nocturnal treatments may be performed daily while the patient is asleep, for approximately six to seven hours.

Nurses can sign up for home therapy RN courses. A home therapy RN course could last for as many as six months. Home therapy nurses can also train home dialysis patients for home hemodialysis. However, as in the previous case, theory and training do not always translate directly to real-world issues, particularly for relatively new nurses. This can increase difficulty for the nurse to do his or her job, and also impact the nurse's ability to train home care patients. Often, nurses may meet different sets of patients with different adverse conditions. Nurses need to be able to adjust treatment parameters according to situations that arise during individual sessions. The nurse needs to handle real-time scenarios in a clinically appropriate fashion. Nurses may also be bombarded with questions from patients regarding programming and other parameters during the session.

The patient's blood may be monitored to determine whether the dialysis has removed enough waste product. A physician may update the treatment parameters to improve dialysis adequacy. However, the blood flow rate cannot be increased indiscriminately. Changing the blood flow rate may depend on factors including the maturity and strength of the patient's vascular access. The clearance may be adjusted by choosing the correct treatment parameters, such as dialyzer type, treatment time, treatment goal, patient's weight, patient conditions, and similar.

User Interface

In an embodiment, the recommended blood flow rate for improved dialysis clearance can be displayed and recommended in the form of a graph on the UI. Once the patient or home therapy nurse confirms the prescription treatment parameters from the EHR on the UI, the values can be predicted by the AI circuit disclosed above. In one example, the UI includes a "smart assist" UI button to display the recommendations on the UI. The treatment parameter prediction (e.g., blood flow rate) can be recommended on the UI during the entire treatment session. When data are displayed in a graphical form, in one embodiment, the highest point on the Y axis signifies the high blood flow rate. The highest point on the X axis signifies the treatment time. The system can display individual blood flow rate or a series of blood flow rates over the period of treatment. In the case of a plurality of blood flow rates, these can be saved as a blood flow rate profile.

In an embodiment, the patient or nurse can click on the blood flow rate points to accept a suggested value. The value can then be set in the treatment parameters, optionally with a double confirmation. The patient or nurse can also overwrite the blood flow rate suggestion with an edit option. For example, the patient can "drag" blood flow rate points to change the blood flow rate at a particular time in the course of treatment. If the patient is in doubt, the patient or nurse can check the profile, such as a stored profile, to decide on a course of treatment.

Advantageously, this reduces the cognitive load on the user. The system provides an option to save blood flow rate profiles for a patient on the hemodialysis device or a patient card. The saved profile in the patient card can be viewed or reviewed by a nephrologist or other doctor at the next appointment, and a prescription can be adjusted as necessary. This gives the nephrologist the ability to decide on the treatment parameters, without needing to skim through numerous data. The blood flow rate profiles or the recommended values might be logged for each treatment. These logs might be helpful in improving the AI model, and in some cases, results of treatment can be uploaded back to the cloud for further analysis by the smart software module. In some embodiments, these data are anonymized so that patient privacy is not compromised.

In the event of an adverse condition, a blood flow rate might be suggested to the user. Accepting this value during treatment can result in a dynamic suggestion or a change in blood flow rate instantaneously.

In an embodiment, the AI circuit can also have an interface to a voice-activated user prompt for patients with hearing and cognitive impairments. This can allow voice control to further ease patient operation.

Example User Interface Outputs

Figure 4:
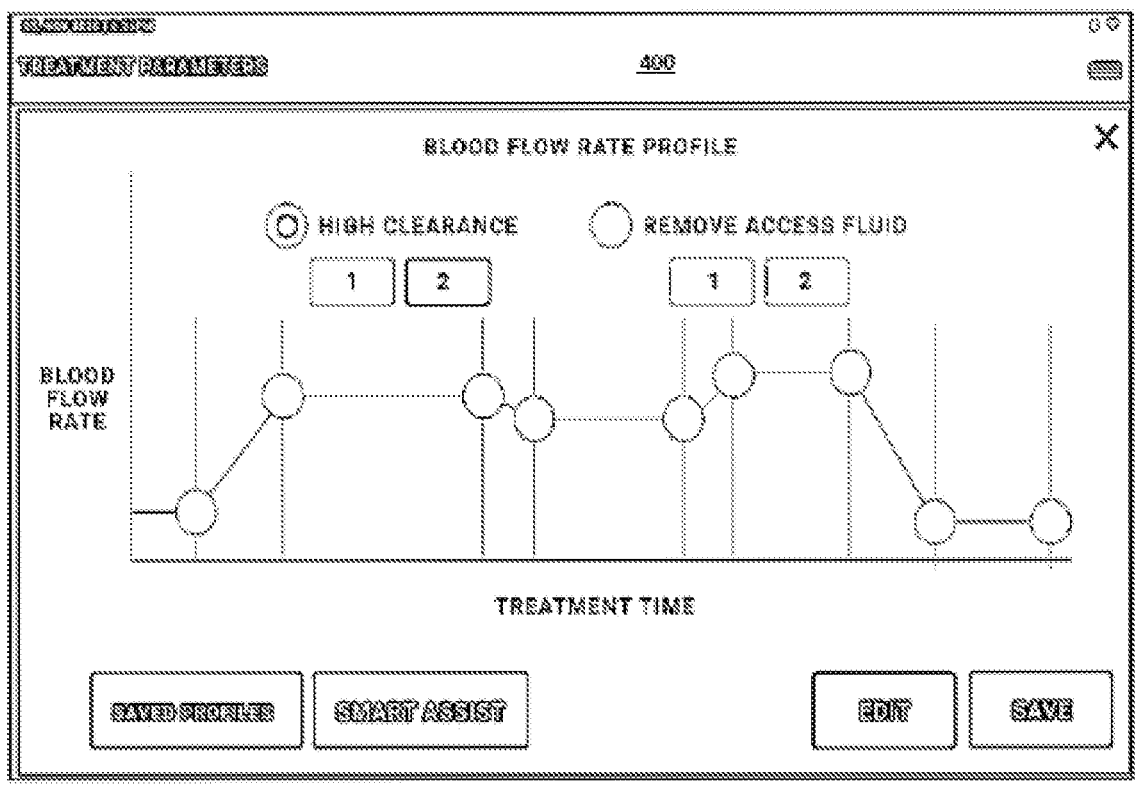
FIGS. 4 and 5 illustrate example outputs that can be provided on a user interface.
Figure 5:
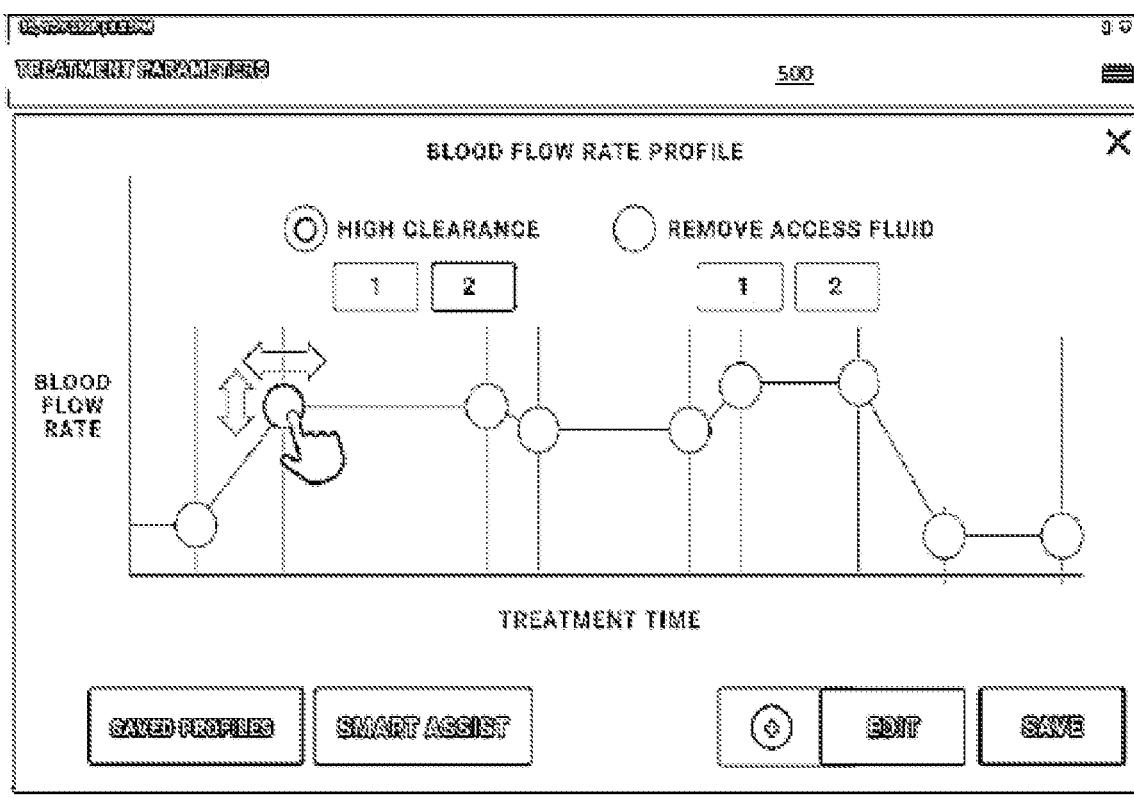

FIGS. 4 and 5 illustrate example outputs that can be provided on a user interface, as disclosed herein.

In the example of FIG. 4, user interface 400 provides a recommendation for a blood flow rate for high clearance for the device. This recommendation can be derived, for example, from an AI engine. The recommendation provides a blood flow rate profile that starts with a relatively low blood flow rate, ramps up to an intermediate blood flow rate at the beginning of treatment, reaches a peak approximately three-quarters through the treatment, and then ramps down to a relatively low blood flow rate at the end of treatment. In some cases, the user can operate the illustrated smart assist button to request a recommended blood flow rate.

As illustrated in FIG. 5, the user can accept the recommended blood flow rate displayed on user interface 500, or in some cases, as in the case of a touchscreen, the user can operate the touchscreen to change the recommended profile. For example, the user can operate the edit button illustrated, to edit the recommended blood flow rate. The user can then move individual points up and down, or left and right, to change the blood flow rate represented, and/or to change when that blood flow rate is used during the treatment. The user can then use the save button to save the selected blood flow rate.

Cloud Service and Medical Device Interaction

Figure 6:
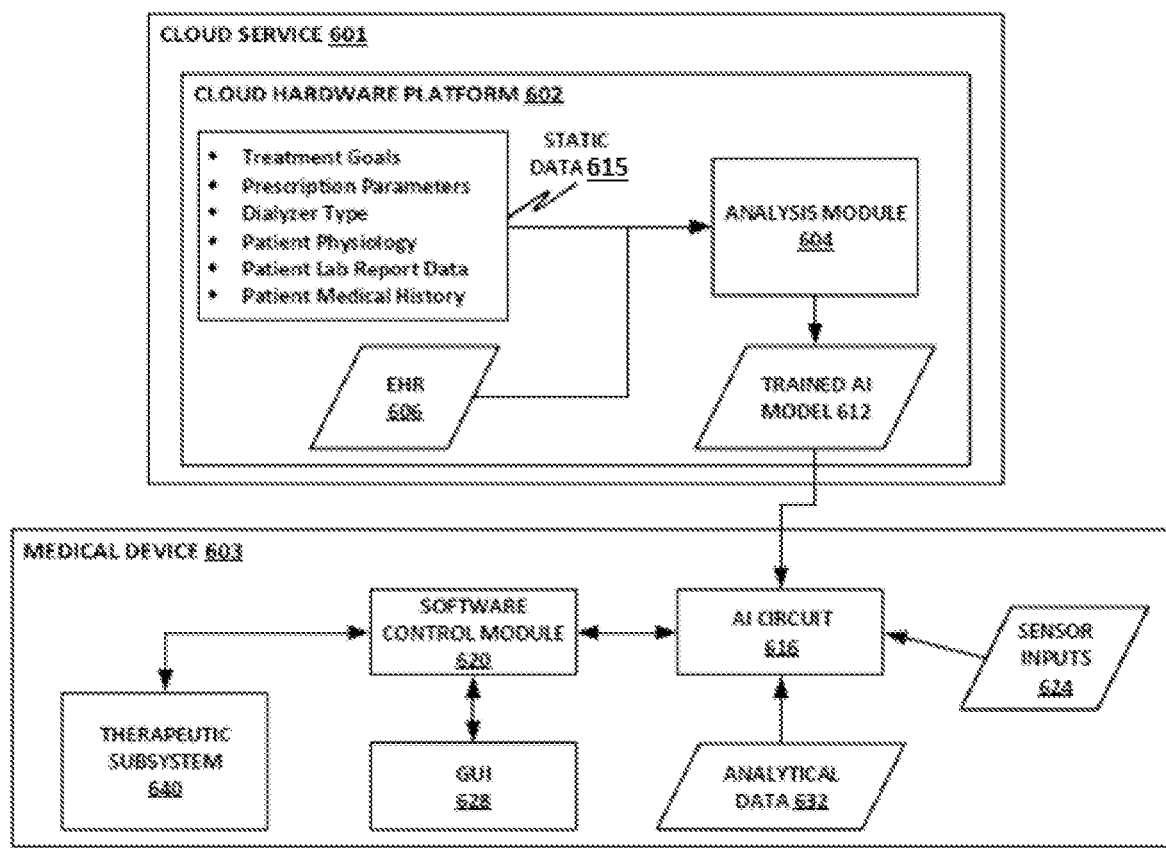
FIG. 6 is a block diagram illustrating interaction between a cloud service and a medical device.

FIG. 6 is a block diagram illustrating interaction between a cloud service 601 and a medical device 603. In this example, cloud service 601 provides a trained or preprocessed AI model to medical device 603.

Cloud service 601 includes a cloud hardware platform 602, that collects various data referred to herein as static data 615. Static data 615 are so labeled because they are relatively static compared to the real-time, or near real-time, treatment data, which can change continuously during the course of treatment. In contrast, the static data are not expected to change during the course of treatment. Static data can include, by way of illustrative and nonlimiting example, treatment goals, prescription parameters, dialyzer type, patient physiology, patient lab report data, and patient medical history. Static data 615 can also be combined with EHR 606, which can contain historical patient data. These can then be provided to analysis module 604. Analysis module 604 can analyze static data 615 and EHR data 606, along with any other data that can be provided, such as data that are more applicable to a general population or class of people. Analysis module 604 uses these to create a trained or otherwise prepared AI model 612. Trained AI model 612 is ready to be run on an endpoint device, such as a specific medical device. In this example, trained AI model 612 is specific to the individual patient and the treatment conditions.

Analytical data for trained AI model 612 may be obtained, for example, by lab regression testing of various treatment parameters, physiological parameters, and adverse condition combinations. The resultant clinical outputs may be based on various patient data and biochemically-fabricated samples. The treatment parameters may include, by way of illustrative and nonlimiting example, prescribed blood flow rate, treatment time, treatment goal, fluid to be removed, patient conditions, dialyzer types used, vascular access type, patient's age and gender, patient physiological conditions, and patient treatment logs. The clinical output data might include urea removed ratio/percentage and Kt/V over a period The input for the AI engine may include data analytics from software control module 620, and current treatment parameters entered on the user interface, or alternatively obtained in safe encrypted form from a cloud-based EHR service and/or picture archiving and communication system (PACS).

The proposed AI may then compare the smart therapy and the current EHR data to provide optimal high clearance predictions and recommendations ranges for the treatment parameters.

For example, the AI system may compare current EHR details (entered on the UI or retrieved from a service) against laboratory results data analytics, and a learning regression model from history data. The result may be a recommendation for critical treatment parameter adjustment for high clearance. Hyperparameter tuning may occur as part of the learning regression model.

The AI model predictions and recommendations may be gathered, in at least one embodiment, by using a machine learning regression model. The regression model may identify patterns and relations between different combination of data.

During a new treatment session, AI circuit 616 of medical device 603 may suggest appropriate treatment parameters for high clearance and overall clinical output of the session.

Trained AI model 612 is provided to medical device 603, which uses AI circuit 616 to process trained AI model 612. AI circuit 616 receives sensor inputs 624, such as via smart sensors connected to the home (e.g., smart scales, smart BP monitors, smart pulse oximeters, or other smart sensors), as well as manual user inputs, as necessary. AI circuit 616 also receives analytical data 632. Together, these form the inputs to AI circuit 616, which provides recommendations to software control module 620. Software control module 620 provides inputs and outputs to GUI 628, which can provide the recommendation to a user, and can receive an indication of whether the user has accepted the recommendation. Software control module 620 can then control therapeutic subsystem 640.

Method (As Performed, for Example, by a Cloud Service)

Figure 7:
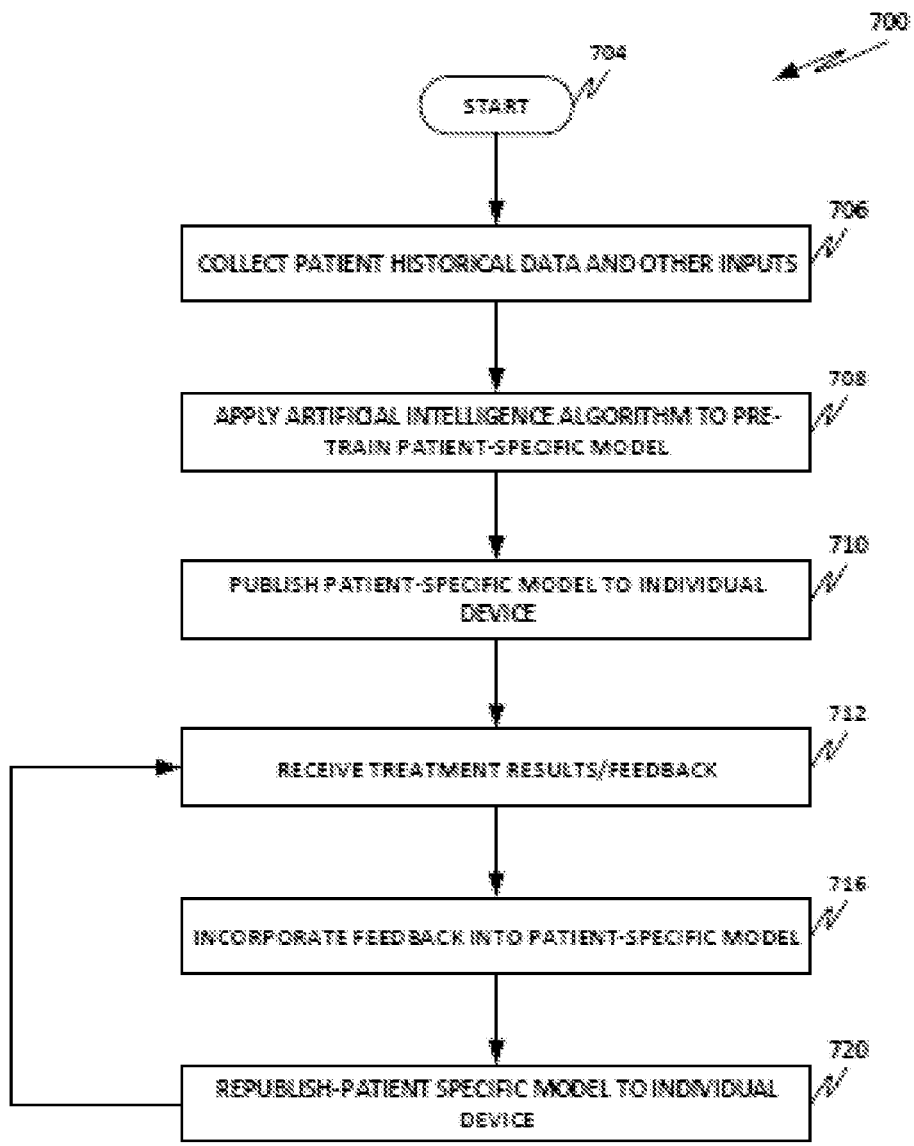
FIG. 7 is a flowchart of a method.

FIG. 7 is a flowchart of a method 700. Method 700 can be performed, for example, by a cloud service.

The method starts in block 704.

In block 706, the system collects patient historical data and other inputs that can be used to train or refine a model.

In block 708, the system applies an AI algorithm to pre-train a patient-specific model.

In block 710, the system publishes the patient-specific model to an individual device, such as by transferring the model via a secure network connection to the individual device.

In block 712, the system can receive treatment results or feedback from the individual device. These can also be received via a secure network connection.

In block 716, the system can optionally incorporate the feedback into the patient-specific model, and/or into more general models applicable to other patients.

In block 720, the system can republish the patient-specific model to the individual device. This republished model can include the incorporated feedback, and optionally, improvements derived from other patient data. The process of improvement can then continue in a loop between blocks 712 and 720.

Method (as Performed, for Example, by an Individual Therapeutic Device)

Figure 8:
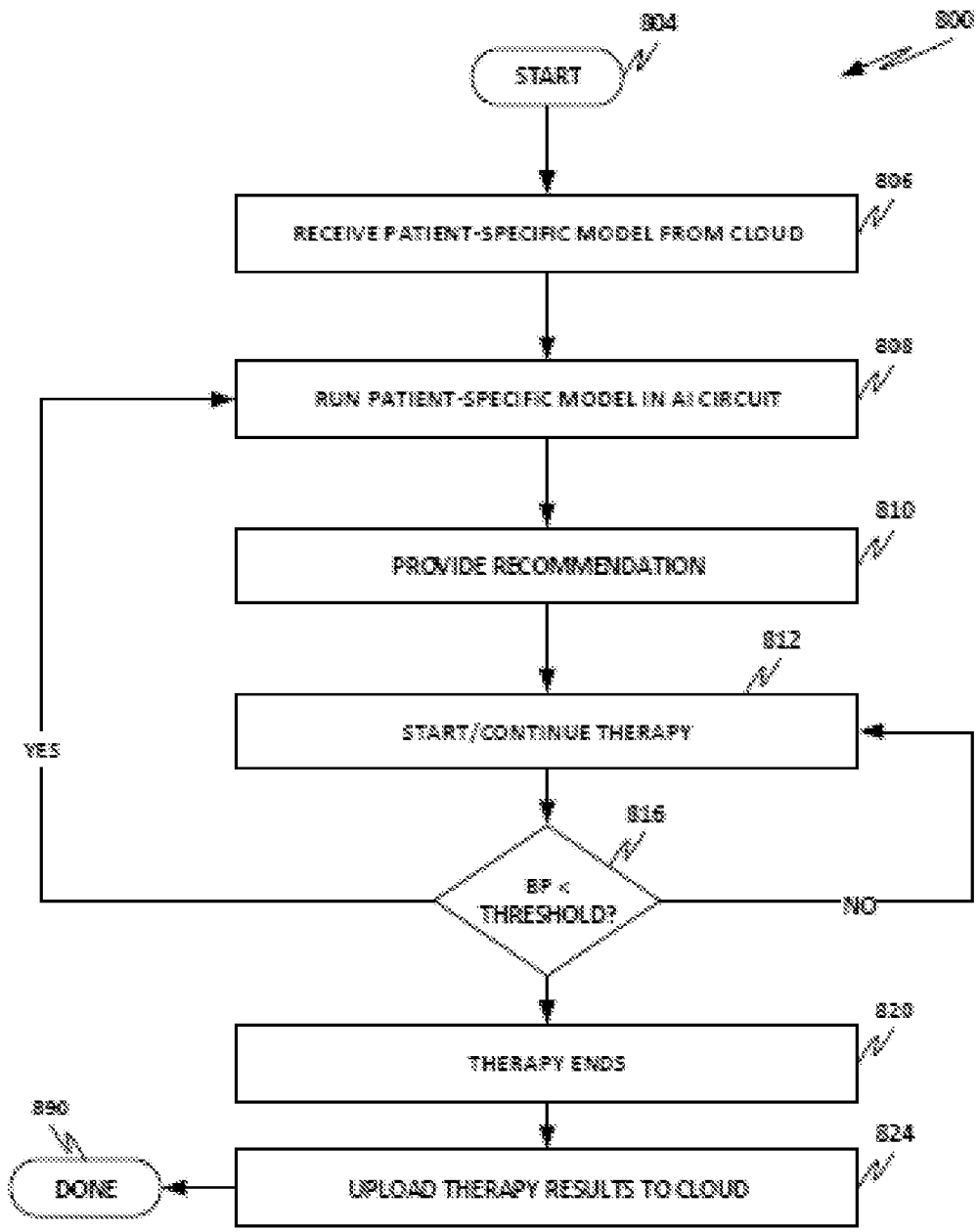
FIG. 8 is a flowchart of an additional method.

FIG. 8 is a flowchart of a method 800. Method 800 can be performed by the individual therapeutic device, such as a hemodialysis device.

Starting at block 804, in block 806 the system receives the patient-specific model from the cloud. For example, the system can operate a secure network connection to download the patient-specific model from a cloud service.

In block 808, the system runs the patient-specific model in a programmable circuit, such as an AI circuit.

In block 810, either autonomously or in response to a stimulus, such as the user pressing a smart assist button, the system provides a recommendation. The recommendation can include a suggested flow rate, or a suggested flow rate profile, by way of nonlimiting example.

In block 812, therapy commences. As therapy continues, the system can continuously monitor the patient to ensure that safety is maintained. For example, increasing the blood flow rate too high can help to increase clearance, but could cause the patient's blood pressure to drop dangerously low. Thus, in this example, a blood pressure sensor is used to monitor the patient's blood pressure. In other embodiments, other sensors could be used to monitor other parameters.

In decision block 816, if the blood pressure drops below a threshold, then control returns to block 808, where the system can use this new input to recalculate a recommended blood flow profile. The user can be given an opportunity to accept or reject this recommendation, unless the blood pressure drops dangerously low, in which case an automatic override can occur.

If the blood pressure remains above the threshold, then looping back to block 812, therapy continues until the therapy is complete.

In block 820, the therapy ends. For example, block 820 can represent the end of a 3-to-4-hour hemodialysis session.

In block 824, optionally, the patient's therapeutic results from this session can be uploaded back to the cloud service to help further improve the model. Note that for the purpose of improving a patient-specific model, the therapeutic results should be associated with the individual patient. However, one of skill will understand that the data can be aggregated from one or more patients to improve the general model. The data can be anonymized to preserve patient privacy.

In block 890, the method is done.

Network Function Virtualization (NFV) Infrastructure

Figure 9:
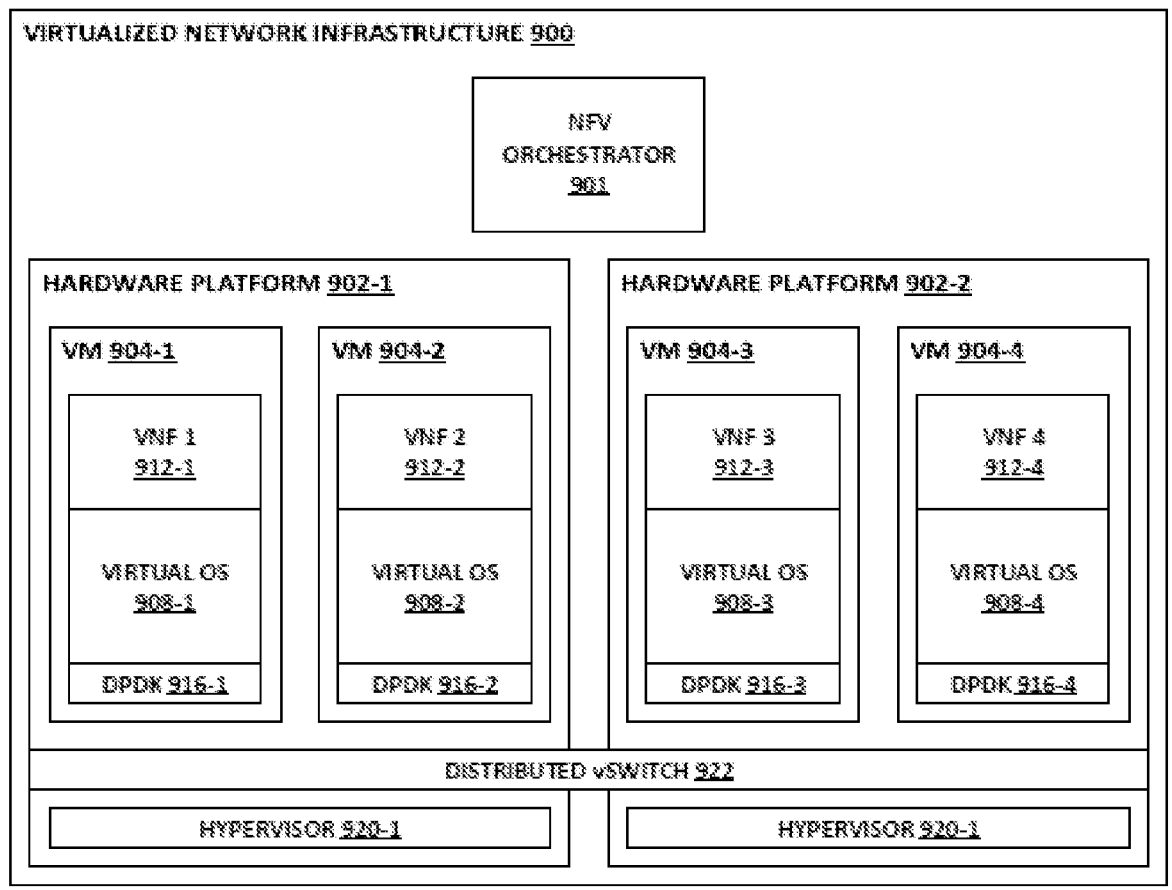
FIG. 9 is a block diagram of a network function virtualization (NFV) infrastructure.

FIG. 9 is a block diagram of an NFV infrastructure 900. FIG. 9 illustrates a platform for providing virtualization services. Virtualization can be used in some embodiments to provide one or more features of the present disclosure.

NFV is an aspect of network virtualization that is generally considered distinct from, but that can still interoperate with, software-defined networking (SDN). For example, virtual network functions (VNFs) can operate within the data plane of an SDN deployment. NFV was originally envisioned as a method for providing reduced capital expenditure (Capex) and operating expenses (Opex) for telecommunication services.

One feature of NFV is replacing proprietary, special-purpose hardware appliances with virtual appliances running on commercial off-the-shelf (COTS) hardware within a virtualized environment. In addition to Capex and Opex savings, NFV provides a more agile and adaptable network. As network loads change, VNFs can be provisioned ("spun up") or removed ("spun down") to meet network demands. For example, in times of high load, more load balancing VNFs can be spun up to distribute traffic to more workload servers (which can themselves be virtual machines). In times when more suspicious traffic is experienced, additional firewalls or deep packet inspection (DPI) appliances can be needed.

Because NFV started out as a telecommunications feature, many NFV instances are focused on telecommunications. However, NFV is not limited to telecommunication services. In a broad sense, NFV includes one or more VNFs running within a network function virtualization infrastructure (NFVI), such as NFVI 900. Often, the VNFs are inline service functions that are separate from workload servers or other nodes. These VNFs can be chained together into a service chain, which can be defined by a virtual subnetwork, and which can include a serial string of network services that provide behind-the-scenes work, such as security, logging, billing, and similar.

In the example of FIG. 9, an NFV orchestrator 901 manages a number of the VNFs 912 running on an NFVI 900. NFV requires nontrivial resource management, such as allocating a very large pool of compute resources among appropriate numbers of instances of each VNF, managing connections between VNFs, determining how many instances of each VNF to allocate, and managing memory, storage, and network connections. This can require complex software management, thus making NFV orchestrator 901 a valuable system resource. Note that NFV orchestrator 901 can provide a browser-based or graphical configuration interface, and in some embodiments can be integrated with SDN orchestration functions.

Note that NFV orchestrator 901 can be virtualized (rather than a special-purpose hardware appliance). NFV orchestrator 901 can be integrated within an existing SDN system, wherein an operations support system (OSS) manages the SDN. This can interact with cloud resource management systems (e.g., OpenStack) to provide NFV orchestration. An NFVI 900 can include the hardware, software, and other infrastructure to enable VNFs to run. This can include a hardware platform 902 on which one or more VMs 904 can run. For example, hardware platform 902-1 in this example runs VMs 904-1 and 904-2. Hardware platform 902-2 runs VMs 904-3 and 904-4. Each hardware platform can include one or more hypervisor 920-1, virtual machine manager (VMM), or similar function, which can include and run on a native (bare metal) operating system, which can be minimal so as to consume very few resources.

Hardware platforms 902-1 or 902-2 can be or comprise a rack or several racks of blade or slot servers (including, e.g., processors, memory, and storage), one or more data centers, other hardware resources distributed across one or more geographic locations, hardware switches, or network interfaces. An NFVI 900 can also include the software architecture that enables hypervisors to run and be managed by NFV orchestrator 901.

Running on NFVI 900 are a number of VMs 904, each of which in this example is a VNF providing a virtual service appliance. Each VM 904 in this example includes an instance of the Data Plane Development Kit (DPDK), a virtual operating system 908, and an application providing the VNF 912 including VNF-1 912-1, VNF-2 912-2, VNF-3 912-3, VNF-4 912-4. Any number of additional VNF can be provided, as required. The virtual operating system 908 can include Virtual OS 908-1, Virtual OS 908-2, Virtual OS 908-3, Virtual OS 908-4, or any number of additional virtual operating systems as required.

Virtualized network functions could include, as nonlimiting and illustrative examples, firewalls, intrusion detection systems, load balancers, routers, session border controllers, DPI services, network address translation (NAT) modules, or call security association.

The illustration of FIG. 9 shows that a number of VNFs 912 have been provisioned and exist within NFVI 900. FIG. 9 does not necessarily illustrate any relationship between the VNFs and the larger network, or the packet flows that NFVI 900 can employ.

The illustrated collective DPDK instances 916-1, 916-2, 916-3, and 916-4 provide a set of optimized libraries for communicating across a virtual switch (vSwitch) 922. DPDK 916-1 and DPDK 916-2 can be associated with hardware platform 902-1. DPDK 916-3 and DPDK 916-4 can be associated with hardware platform 902-2. Like VMs 904-3 and 904-4, switch 922 can be provisioned and allocated by a hypervisor 920-1. The hypervisor uses a network interface to connect the hardware platform to the data center fabric (e.g., a host fabric interface (HFI)). This HFI can be shared by all VMs 904-1, 904-2, 904-3, and 904-4 running on the hardware platform 902-1 or hardware platform 902-2. Thus, the vSwitch can be allocated to switch traffic between VMs 904. The vSwitch can be a pure software vSwitch (e.g., a shared memory vSwitch), which can be optimized so that data are not moved between memory locations, but rather, the data can stay in one place, and pointers can be passed between VMs 904 to simulate data moving between ingress and egress ports of the vSwitch. The vSwitch can also include a hardware driver (e.g., a hardware network interface intellectual property (IP) block that switches traffic, but that connects to virtual ports rather than physical ports). In this illustration, a distributed vSwitch 922 is illustrated, wherein vSwitch 922 is shared between two or more physical hardware platforms 902.

One skilled in the art will understand that various combinations and/or modifications and variations can be made in the described systems and methods depending upon the specific needs for operation. Various aspects disclosed herein can be combined in different combinations than the combinations specifically presented in the description and accompanying drawings. Moreover, features illustrated or described as being part of an aspect of the disclosure can be used in the aspect of the disclosure, either alone or in combination, or follow a preferred arrangement of one or more of the described elements. Depending on the example, certain acts or events of any of the processes or methods described herein can be performed in a different sequence, can be added, merged, or left out altogether (e.g., certain described acts or events cannot be necessary to carry out the techniques). In addition, while certain aspects of this disclosure are described as performed by a single module or unit for purposes of clarity, the techniques of this disclosure can be performed by a combination of units or modules associated with, for example, a device.

What is claimed is:

1. A medical device, comprising:
 a therapeutic subsystem to deliver a medical therapy, including a sensor to monitor a biometric health factor;
 a user interface;
 a controller, including a processor and a memory;
 therapy software comprising instructions encoded within the memory to instruct the processor to receive a prescribed therapy, to receive a therapeutic setting recommendation, and to display the therapeutic setting recommendation to an operator via the user interface;
 a network interface, and instructions to receive, via the network interface, a prepared artificial intelligence (AI) model from a cloud service; and
 an AI circuit having execution hardware comprising at least one logic gate, and further comprising instructions to instruct the execution hardware to execute the prepared AI model to provide a recommended therapy setting for the therapeutic subsystem, wherein the AI circuit is incorporated into the prepared AI model data from the sensor.

2. The medical device of claim 1, wherein the execution hardware includes the processor.

3. The medical device of claim 1, wherein the medical device is selected from an insulin pump, a continuous positive airway pressure machine, an external neural stimulator, an intravenous fluid device, and a dialysis machine.

4. The medical device of claim 1, wherein the medical device is a dialysis machine.

5. The medical device of claim 4, wherein the prepared AI model incorporates input selected from analytical data from laboratory testing, historical treatment parameters, patient access type, dialyzer type, therapy method, patient condition, fluid removal, dialyzer permeability, patient weight, dry weight, treatment time, and treatment goal.

6. The medical device of claim 4, wherein the therapy setting recommendation comprises a blood flow rate recommendation.

7. The medical device of claim 6, wherein the therapy software instructions are further to automatically select a recommended blood flow rate.

8. The medical device of claim 6, wherein the therapy software instructions are further to detect a changed blood flow rate during therapy, and wherein the AI circuit is further to predict a recommendation according to the changed blood flow rate.

9. The medical device of claim 6, wherein the sensor detects an adverse condition, and wherein the AI circuit recommends a blood flow rate according to the adverse condition.

10. The medical device of claim 9, wherein the adverse condition includes low patient blood pressure.

11. The medical device of claim 6, wherein the therapy software instructions are further to save one or more blood flow rate profiles for a patient.

12. The medical device of claim 4, wherein the therapeutic setting recommendation is selected from blood flow rate, sodium profile, and ultrafiltration rate profile.

13. The medical device of claim 1, wherein the user interface includes a control to request a therapeutic setting recommendation.

14. The medical device of claim 1, wherein the user interface includes one or more controls to automatically accept or reject recommended therapeutic settings.

15. The medical device of claim 1, wherein the therapy software instructions are further to download the treatment parameters from a cloud service.

16. The medical device of claim 1, wherein the AI circuit is to provide a high clearance prediction.

17. The medical device of claim 1, wherein the AI circuit is further to concurrently provide a plurality of recommended therapeutic settings.

18. The medical device of claim 1, wherein the AI circuit provides an AI model selected from the group consisting of linear regression, logistic regression, linear discriminant analysis, decision tree, naïve Bayes, k-nearest neighbors, learning vector quantization, support vector machine, random forest, neural network, convolutional neural network, and deep neural network.

19. A system, comprising the medical device of claim 1, and further comprising a cloud service, the cloud service comprising a hardware platform comprising a processor and a memory, and instructions encoded within the memory to instruct the processor to receive a plurality of historical patient inputs and build the prepared model from the plurality of historical patient inputs.

20. The system of claim 19, wherein the prepared model is a patient-specific model.

* * * * *